(12) United States Patent
Tocilj et al.

(10) Patent No.: US 10,245,320 B2
(45) Date of Patent: Apr. 2, 2019

(54) IMMUNOMODULATORY PHARMACEUTICAL COMPOSITIONS AND METHODS OF USE THEREOF

(71) Applicant: Enzo Biochem, Inc., New York, NY (US)

(72) Inventors: Ante Tocilj, Syosset, NY (US); Jack Coleman, East Northport, NY (US); Elazar Rabbani, New York, NY (US); James J. Donegan, Long Beach, NY (US)

(73) Assignee: Enzo Biochem, Inc., New York, NY (US)

( * ) Notice: Subject to any disclaimer, the term of this patent is extended or adjusted under 35 U.S.C. 154(b) by 0 days.

(21) Appl. No.: 15/719,821

(22) Filed: Sep. 29, 2017

(65) Prior Publication Data

US 2018/0303932 A1    Oct. 25, 2018

Related U.S. Application Data

(60) Provisional application No. 62/402,248, filed on Sep. 30, 2016, provisional application No. 62/535,047, filed on Jul. 20, 2017.

(51) Int. Cl.
*A61K 39/39*         (2006.01)
*A61K 39/00*         (2006.01)

(52) U.S. Cl.
CPC .......... *A61K 39/39* (2013.01); *A61K 39/0008* (2013.01); *A61K 39/0011* (2013.01); *A61K 2039/55516* (2013.01)

(58) Field of Classification Search
None
See application file for complete search history.

(56) References Cited

U.S. PATENT DOCUMENTS

| | | | |
|---|---|---|---|
| 5,190,859 | A | 3/1993 | Dustin et al. |
| 5,728,677 | A | 3/1998 | Wallner et al. |
| 5,955,077 | A | 9/1999 | Andersen et al. |
| 6,991,797 | B2 | 1/2006 | Andersen et al. |
| 7,575,870 | B1 | 8/2009 | Lalvani et al. |
| 7,632,646 | B1 | 12/2009 | Lalvani et al. |
| 2008/0014194 | A1 | 1/2008 | Schenk et al. |
| 2014/0241984 | A1 | 8/2014 | El-Agnaf |

OTHER PUBLICATIONS

Abd-Elhadi et al., "Total and Proteinase K-Resistant α-Synuclein Levels in Erythrocytes, Determined by their Ability to Bind Phospholipids, Associate with Parkinson's Disease," *Scientific Reports*, vol. 5, pp. 1-12 (2015).
Badawy et al., "Extracellular α-Synuclein drives sphingosine 1-phosphate receptor subtype 1 out of lipid rafts, leading to impaired inhibitory G-protein signaling," *J. Biol. Chem.*, vol. 293, No. 21, pp. 8208-8216 (2018).
Bartels et al., "α-Synuclein occurs physiologically as a helically folded tetramer that resists aggregation," *Nature*, vol. 477, pp. 107-111 (2011).
Belknap et al., "Interferon-Gamma Release Assays," *Clin Lab Med*, vol. 34, pp. 337-349 (2014).
Buttari et al., "Crosstalk between Red Blood Cells and the Immune System and Its Impact on Atherosclerosis," *BioMed Research International*, vol. 2015, Article ID 616834, 8 pages (2015).
De Jager et al., "The role of the CD58 locus in multiple sclerosis," *PNAS*, vol. 106, No. 13, pp. 5264-5269 (2009).
Dutta et al., "Latent Tuberculosis Infection: Myths, Models, and Molecular Mechanisms," *Microbiology and Molecular Biology Reviews*, vol. 78, No. 3, pp. 343-371 (2014).
Fauvet et al., "αSynuclein in Central Nervous System and from Erythrocytes, Mammalian Cells, and *Escherichia coli* Exists Predominantly as Disordered Monomer," *Journal of Biological Chemistry*, vol. 287, No. 19, pp. 15345-15364 (2012).
Gould et al., "Evidence of Native α-Synuclein Conformers in the Human Brain," *Journal of Biological Chemistry*, vol. 289, No. 11, pp. 7929-7934 (2014).
Harms, "MHCII is Required for α-Synuclein-Induced Activation of Microglia, CD4 T Cell Proliferation, and Dopaminergic Neurodegeneration," *The Journal of Neuroscience*, vol. 33, No. 23, pp. 9592-9600 (2013).
Jo et al., "αSynuclein Membrane Interactions and Lipid Specificity," *The Journal of Biological Chemistry*, vol. 275, No. 44, pp. 34328-34334 (2000).
Kalechman et al., "Enhancing Effects of Autologous Erythrocytes on Human or Mouse Cytokine Secretion and IL-2R Expression," *Cellular Immunology*, vol. 148, pp. 114-129 (1993).
Kim et al., "Interferon gamma mRNA quantitative real-time polymerase chain reaction for the diagnosis of latent tuberculosis: a novel interferon gamma release assay," *Diagnostic Microbiology and Infectious Disease*, vol. 75, pp. 68-72 (2013).
Lalvani et al., "Rapid Detection of *Mycobaterium tuberculosis* Infection by Enumeration of Antigen-specific T Cells," *Am J Respir Crit Care Med*, vol. 163, pp. 824-828 (2001).
Longhena et al., "The Contribution of α-Synuclein Spreading to Parkinson's Disease Synaptopathy," *Neural Plasticity*, vol. 2017, Article ID 5012129, 15 pages (2015).
Pacheco et al., "An extracellular mechanism that can explain the neurotoxic effects of α-Synuclein aggregates in the brain," *frontiers in Physiology*, vol. 3, Article 297, pp. 1-10 (2012).
Pollock et al., "The Potential of teh ESAT-6 Antigen Secreted by Virulent Mycobacteria for Specific Diagnosis of Tuberculosis," *The Journal of Infectious Diseases*, vol. 175, pp. 1251-1254 (1997).
Rooijen et al., "Lipid bilayer disruption by oligomeric α-Synuclein depends on bilayer charge and accessibility of the hydrophobic core," *Biochimica et Biophysica Acta*, vol. 1788, pp. 1271-1278 (2009).

(Continued)

*Primary Examiner* — John D Ulm
(74) *Attorney, Agent, or Firm* — Paul Diamond, Esq.

(57) ABSTRACT

Provided are immunomodulatory pharmaceutical compositions that include alpha-synuclein, and at least one preselected antigen, such as at least one preselected peptide antigen or immunogen. Also provided are methods for modulating immune activity toward at least one preselected antigen in an at least substantially antigen-specific manner that includes administering such a composition to a human patient or a non-human mammalian subject.

26 Claims, 14 Drawing Sheets

Specification includes a Sequence Listing.

(56) References Cited

OTHER PUBLICATIONS

Shameli et al., "A Critical Role for α-Synuclein in Development and Function of T Lymphocytes," *Immunobiology*, vol. 221, No. 2, pp. 333-340 (2016).

Shams et al., "Characterization of a *Mycobacterium tuberculosis* Peptide That is Recognized by Human CD4+ and DD8+ T Cells in the Context of Multiple HLA Alleles," *The Journal of Immunology*, vol. 173, pp. 1966-1977 (2004).

Theodore et al., "targeted Overexpression of Human α-Synuclein Triggers Microglial Activation and an Adaptive Immune Response in a Mouse Model of Parkinson Disease," *J Neuropathol Exp Neurol*, vol. 67, No. 12, pp. 1149-1158 (2008).

Valdinocci et al., "Potential Modes of Intercellular α-Synuclein Transmission," *Int. J. Mol. Sci.*, vol. 18, No. 469, pp. 1-17 (2017).

Weinreb et al., "NACP, A Protein Implicated in Alzheimer's Disease and Learning, Is Natively Unfolded," *American Chemical Society*, vol. 35, No. 43, pp. 13709-13715 (1996).

Whitworth et al., "IGRAs—The gateway to T cell based TB diagnosis," *Methods*, vol. 61, pp. 52-62 (2013).

Yamashita et al., "A dimeric form of soluble recombinant sheep LFA-3(CD58) inhibits human T-cell proliferation by generating regulatory T cells," *Immunopharmacology*, vol. 37, pp. 209-220 (1997).

Safadi et al., "Induction of oral immune regulation towards liver-extracted proteins for treatment of chronic HBV and HCV hepatitis: results of a phase I clinical trial," *Liver International*, vol. 24, pp. 295-307 (2004).

Mustafa et al., "Multiple Epitopes from the *Mycobacterium tuberculosis* ESAT-6 Antigen are Recognized by Antigen-Specific Human T Cell Lines," *Clinical Infectious Diseases*, vol. 30, Suppl. 3, pp. S201-S205 (2000).

Safadi et al., 'Treatment of Chronic Hepatitis B Virus Infection via Oral Immune Regulation Toward Hepatitis B Virus Proteins, *The American Journal of Gastroenterology*, vol. 98, No. 11, pp. 2505-2515 (2003).

Sharma et al., "Hepatitis B. Virus: Inactive carriers," *Virology Journal*, vol. 2, No. 82, 5 pages (2005).

PCT/US2018/042831—Annex to Form PCT/ISA/206 Communication Relating to the Results of the Partial International Search, 10 pages.

Poncin-Epaillard, "Study of the Adhesion of Neurodegenerative Proteins on Plasma-Modified and Coated Polypropylene Surfaces," *Journal of Biomaterials Science, Polymer Edition*, vol. 23, pp. 1879-1893 (2012).

Notification of Transmittal of the International Search Report and the Written Opinion of the International Searching Authority, or the Declaration for PCT/US2018/042831 (copending ENZ-112 family, member), dated Dec. 4, 2018, 17 pages.

Fractionation of Blood
Whole Blood, Serum, HLA-Containing Fraction

Effect of Whole Blood and Fractions

Allogeneic Blood Treatment

Autologous Blood Treatment

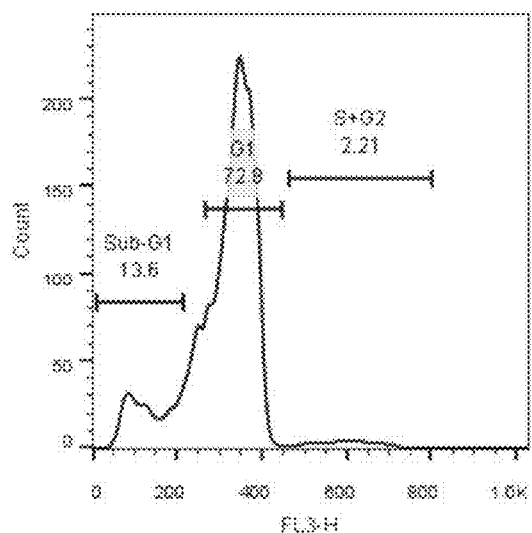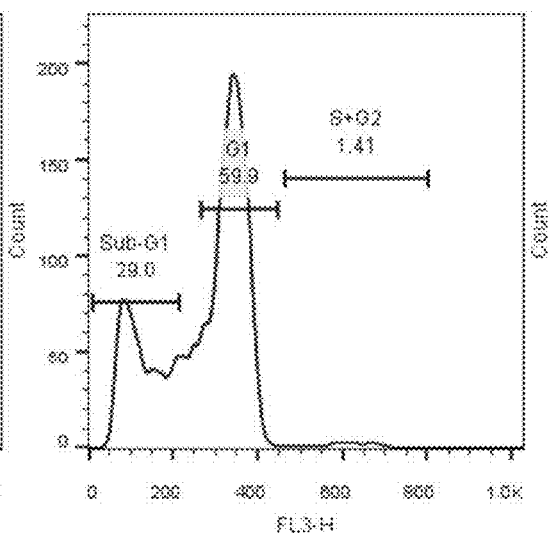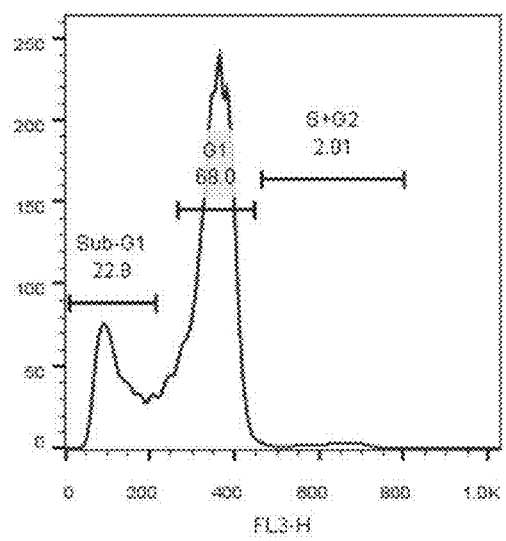
FIG. 4A
FIG. 4B
FIG. 4C

Effects of Immune Enhancer Fraction vs Recombinant HLA and Processed Cells

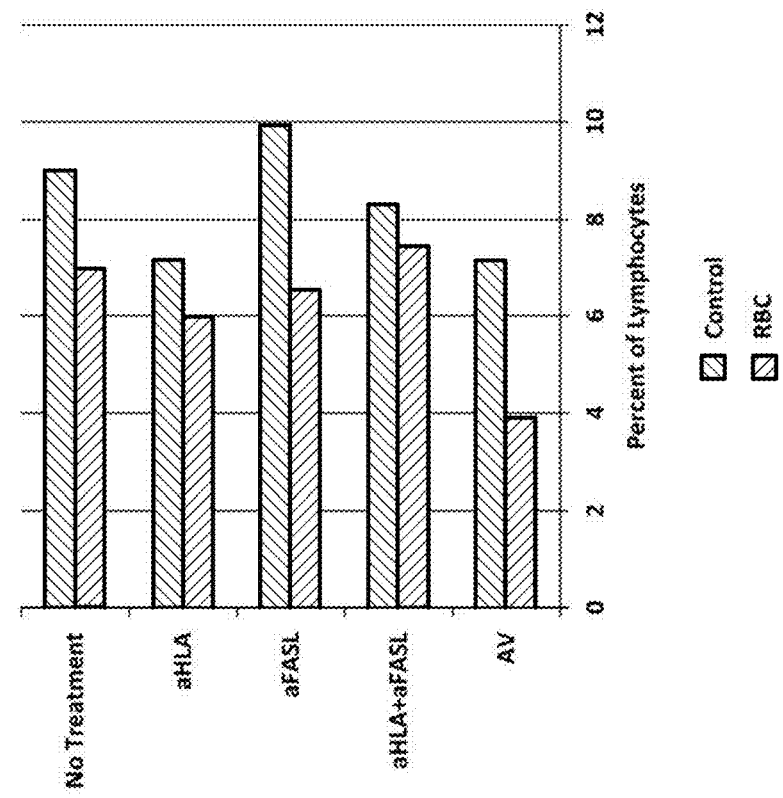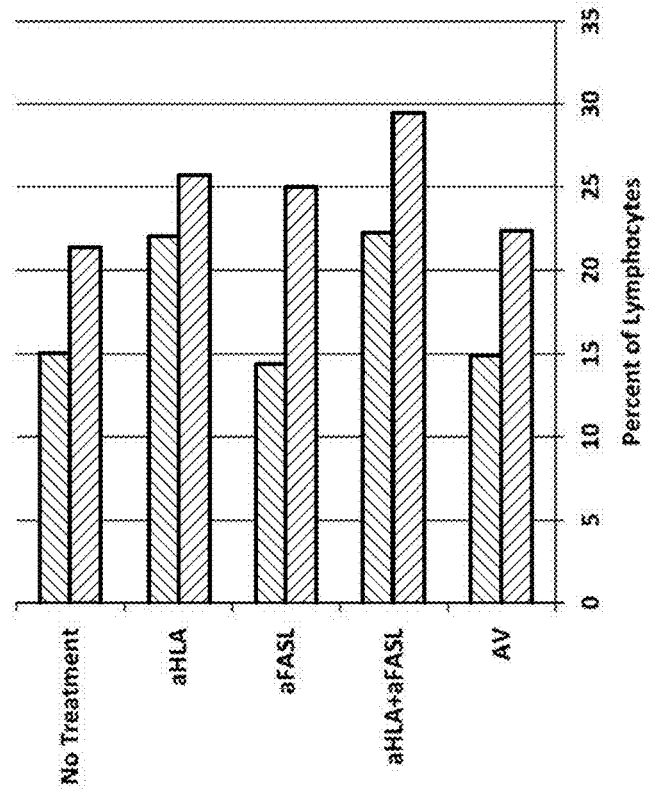
Effects of Various Blocking Factors on Immune Enhancer Fraction Activity
FIG. 6A Sub-G1
FIG. 6B S+G2

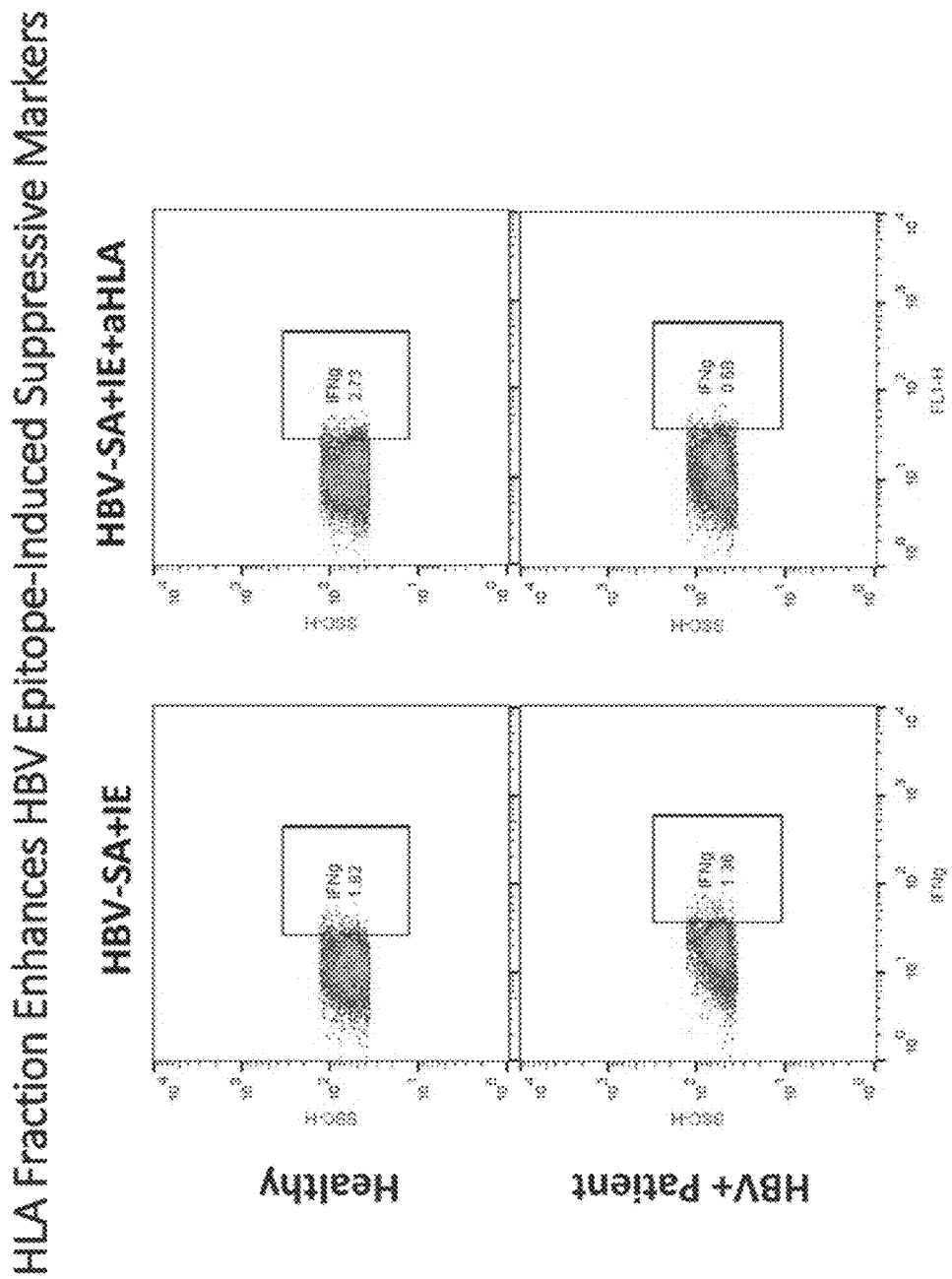

IMMUNOMODULATORY PHARMACEUTICAL COMPOSITIONS AND METHODS OF USE THEREOF

CROSS-REFERENCE TO RELATED APPLICATIONS

This application claims the benefit of U.S. provisional application Ser. No. 62/535,047 filed Jul. 20, 2017 and 62/402,248 filed Sep. 30, 2016, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Sep. 20, 2017, is named ENZ-112-US-SL-ST25.txt and is 45,510 bytes in size.

FIELD OF THE INVENTION

The invention relates to the field of antigen-specific immune modulation.

BACKGROUND

The immune system and its regulation are central to our well-being. A healthy immune system recognizes and eliminates pathogens, pre-cancerous cells and other "non-self" entities, while maintaining a state of non-reactiveness toward normal self cells and tissues. When this state of non-reactiveness to self-antigens breaks down, autoimmune disease may result. Indeed, many chronic inflammatory and tissue-destructive diseases are autoimmune diseases, including, for example, age-related macular degeneration (AMD), uveitis, Crohn's disease, rheumatoid arthritis, systemic lupus erythematosus, and multiple sclerosis. Over eighty autoimmune diseases are known.

What is needed and provided by the present invention are new compositions and methods for modulating immune activity, i.e., for promoting immune reactivity or immune suppressiveness, with respect to preselected antigens.

SUMMARY OF THE INVENTION

One embodiment of the invention provides an immunomodulatory pharmaceutical composition including a mixture of:
 (i) a first component including
  (a) at least partially purified HLA protein or fragments thereof, such as mammalian, for example human,
  (b) whole blood, such as mammalian, for example human, or a cellular fraction thereof, such as a density gradient fraction thereof, such as but not limited to a white blood cell and/or red blood cell (erythrocytes) and/or platelet fraction/layer thereof, or a cell membrane fraction/preparation of any of the foregoing or an extract of any of the foregoing, such as a protein extract, a lipid extract, a carbohydrate extract, a small molecule extract or any combination thereof, and/or
  (c) alpha-synuclein protein, such as mammalian alpha-synuclein protein, such as human alpha-synuclein protein, or fragments thereof; and
 (ii) at least one preselected antigen or immunogen, such as at least one preselected peptide antigen, at least one preselected protein antigen, at least one preselected carbohydrate antigen, at least one preselected lipid antigen, and/or at least one preselected glycolipid antigen.

At least the first component or only the first component may be heat-treated, for example, heat-treated at or above 100° C. for at least 1 or 2 or 3 or 4 or 5 minutes. Heat-treatment may include or consist of autoclaving. The at least partially purified HLA protein or other proteins may be at least substantially denatured. The proteins may at least partially, such as at least substantially, be fragmented into peptides.

For any of the embodiments throughout this disclosure, the antigen or immunogen may be a molecule that is not an HLA molecule and/or is not alpha-synuclein (and/or is not a sequence fragment of either).

The pharmaceutical composition may, for example, be a liquid composition or an at least substantially dry pharmaceutical composition, such as a powder. Dry forms may be prepared by drying a liquid mixture of the components, for example, by lyophilization or any method known in the art. The pharmaceutical composition may include one or more pharmaceutically acceptable excipients.

A related embodiment provides a method for manufacturing an immunomodulatory pharmaceutical composition including the steps of:
 providing a first component including
  (a) at least partially purified HLA protein or fragments thereof, such as mammalian, for example human,
  (b) whole blood, such as mammalian, for example human, or a cellular fraction thereof, such as a density gradient fraction thereof, such as but not limited to a white blood cell and/or red blood cell (erythrocytes) and/or platelet fraction/layer thereof, or a cell membrane fraction/preparation of any of the foregoing or an extract of any of the foregoing, such as a protein extract, a lipid extract, a carbohydrate extract, a small molecule extract or any combination thereof, and/or
  (c) alpha-synuclein protein, such as mammalian alpha-synuclein protein, such as human alpha-synuclein protein, or fragments thereof; and
 providing a second component including at least one preselected antigen or immunogen, such as at least one preselected peptide antigen, at least one preselected protein antigen, at least one preselected carbohydrate antigen, at least one preselected lipid antigen, and/or at least one preselected glycolipid antigen; and
 mixing the first component and the second component, for example, under aqueous conditions.

The method may further include heat-treating at least the first component, such as only the first component prior to the mixing step. The method may include mixing the two components and then heat-treating the mixture. The method may include separately heat-treating the first and second components prior to the mixing step.

The method may further include at least substantially drying the liquid mixture to obtain an at least substantially dry form, such as a powder, by, for example, lyophilizing the liquid mixture or otherwise drying it. One or more excipients may be admixed before and/or after the drying step.

The antigen (or immunogen) may, for example, be a molecule that is not an HLA molecule and/or is not alpha-synuclein. For example, the antigen may be a peptide, such as a synthetic peptide, that is not a sequence fragment of an HLA molecule or alpha-synuclein.

A further embodiment of the invention provides a method for modulating the immune response in a mammal to at least one preselected antigen that includes administering to the mammal an immunomodulatory pharmaceutical composition as described within. Said administration may be parenteral or non-parenteral. The antigen-specific modulation of the immune response may be immunostimulatory or immunosuppressive (tolerogenic).

A further embodiment of the invention provides a method for modulating the immune response in a mammal to at least one preselected antigen that includes:
  coadministering to the mammal:
    (i) one or more of
      (a) at least partially purified HLA protein or fragments thereof, such as mammalian, for example human,
      (b) whole blood, such as mammalian, for example human, or a cellular fraction thereof, such as a density gradient fraction thereof, such as but not limited to a white blood cell and/or red blood cell (erythrocytes) and/or platelet fraction/layer thereof, or a cell membrane fraction/preparation of any of the foregoing or an extract of any of the foregoing, such as a protein extract, a lipid extract, a carbohydrate extract, a small molecule extract or any combination thereof, and
      (c) alpha-synuclein protein, such as mammalian alpha-synuclein protein, such as human alpha-synuclein protein, or fragments thereof; and
    (ii) at least one preselected antigen or immunogen, such as at least one preselected peptide antigen, at least one preselected protein antigen, at least one preselected carbohydrate antigen, at least one preselected lipid antigen, and/or at least one preselected glycolipid antigen.

Any one or more of the compositions under (i) may be treated, such as heat-treated, in any of the manners previously described herein.

Other objects and advantages of the invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE DRAWINGS

FIGS. 4A-C show the effect of control (FIG. 4A), recombinant HLA-B protein (rHLA-B; FIG. 4B), and recombinant HLA-G protein (rHLA-G; FIG. 4C) on the cell cycle distribution of PBMCs, indicating apoptosis-inducing activity of the rHLA-G and rHLA-B proteins on the PBMCs.

FIGS. 6A and 6B show the effect of various blocking factors on the ability of the immune enhancer (heat-treated RBC fraction from density gradient separation) to affect the percentage of PBMCs in the sub-G1 phase (FIG. 6A; indicative of apoptosis induction) and the S+G2 phase (FIG. 6B; indicative of proliferation).

" FIG. 8B) alone, and HBV-A plus IE (FIG. 8C) on PBMCs from healthy human subjects (top panels) and HBV patients (bottom panels).

FIGS. 13A and 13B show the effect of HBV-SA plus IE (FIG. 13A) and HBV-SA plus IE plus anti-HLA class I antibody (aHLA) on the expression of gamma interferon (IFNg) in PBMCs from healthy human subjects (top panels) and HBV patients (bottom panels).

DETAILED DESCRIPTION

Figure 1A:
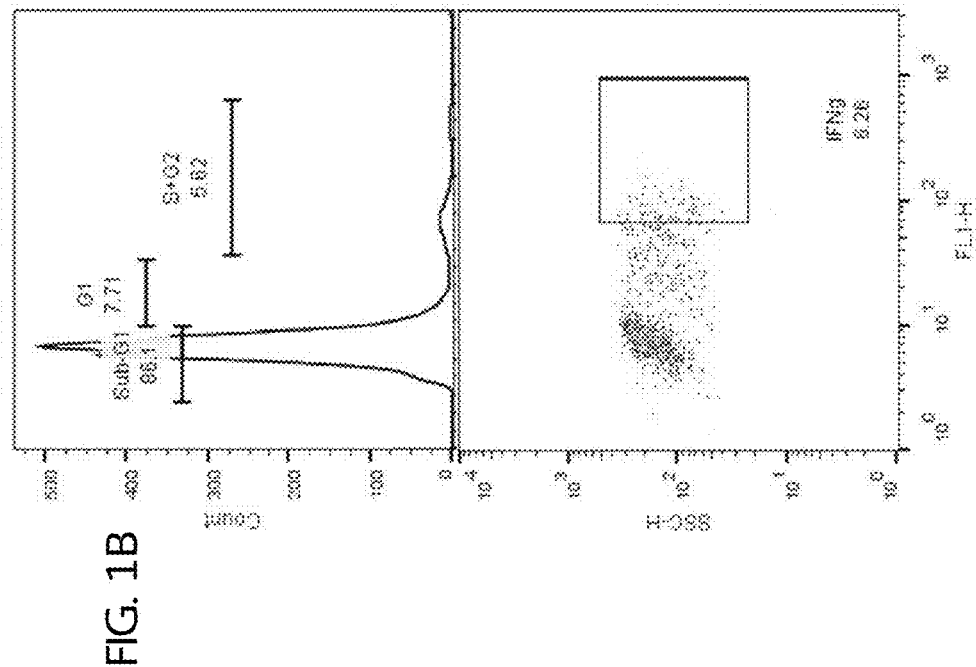
FIGS. 1A and 1B show the effects of a null control treatment on healthy PBMCs (FIG. 1A) and the effect of heat-treated whole blood on PBMCS (FIG. 1A), respectively, both with no added antigens/epitopes, with the top panels showing the cell cycle distribution of treated cells and the bottom panels showing the expression of gamma-interferon (IFNg) in treated cells.

One aspect of the invention is based on the inventors' discovery that heat-treated blood (HTB) can modulate immune responses to antigens. When investigating the combination of HTB and HBsAg with PBMCs from HBV infected patients, the response to HBsAg alone was limited, but when HTB was added, a much stronger response was seen. The effect is antigen specific since HTB by itself gave no response. This result remains unchanged whether the blood is from an autologous or heterologous source, or even from the pooled blood of multiple donors, meaning HTB used to treat patients could be either from the patient themselves which they could donate before the study begins, or as an off-the-shelf reagent from allogeneic donors.

Through ficoll density gradient separation, it was found that the active factor or factors are present in at least the red blood cell (RBC) layer of blood. Soluble (recombinant) HLA was shown to have a similar effect. In in vitro experiments on PBMCs, heat-treated soluble HLA gave similar results as both heat-treated whole blood and the heat-treated RBC density gradient fraction. The effect with the HLA was not as strong as with the heat treated whole blood or that with the heat treated RBC fraction, possibly indicating other contributory factors or the presence of a concentration effect. It was further discovered that the heat treatment increases the effectiveness of the soluble HLA as an immune enhancer.

Heat treatment may, for example, be performed at a temperature of at least 95° C., such as at least 100° C., such as at least 110° C., such as at least 120° C. for at least 1 minute, such as but not limited to 1 minute, at least 15 minutes or 15 minutes, at least 20 minutes or 20 minutes, at least 25 minutes or 25 minutes, or at least 30 minutes or 30 minutes. Heat treatment may, for example be conducted at a temperature in the range of 100-130° C. Heat treatment may include or consist of autoclaving, for example, for 1 minute to three hours, such as 1-30 minutes, such as 5-25 minutes, such as 10-20 minutes, or any subrange or number of minutes within said ranges.

The dose, such as daily dose, of heat-treated blood or blood fraction may, for example, be in the range of 0.5 mg to 5 grams or any amount or subrange of amounts therein, such as 0.5 to 100 mg or 1.0 to 50 mg. Heat treatment may, for example, be performed by autoclaving the material. The dose of a protein of a protein or protein extract of the blood or blood fraction or purified or recombinant HLA protein (or fragments thereof) or purified or recombinant alpha-synuclein protein (or fragments thereof) may, for example, be in the range of 100 micrograms to 20 mg or any subrange therein such as 0.5 to 5 mg.

Dosing may, for example, be performed daily, every other day, every three days, biweekly or weekly.

Various aspects of the invention are further illustrated by the appended drawings and experimental results shown therein. Blood products indicated were made from human whole blood or blood fractions. Blood fractions were isolated by ficol gradient centrifugation using Histopaque (Sigma) and collecting either the RBC or serum fractions as indicated in each experiment. The whole blood or fraction was then autoclaved for 20 minutes, then resuspended to twice their original volume using PBS and sonicated for 30 minutes to restore solubility. PBMCs which had been frozen in liquid nitrogen were thawed, washed in RPMI 1640, then resuspended in RPMI 1640 complete medium, treated as indicated, and incubated for between 16 and 72 hours for use, depending on the experiment. Cells were then collected and stained as indicated, and run in a FACS Calibur flow cytometer.

Figure 1B:
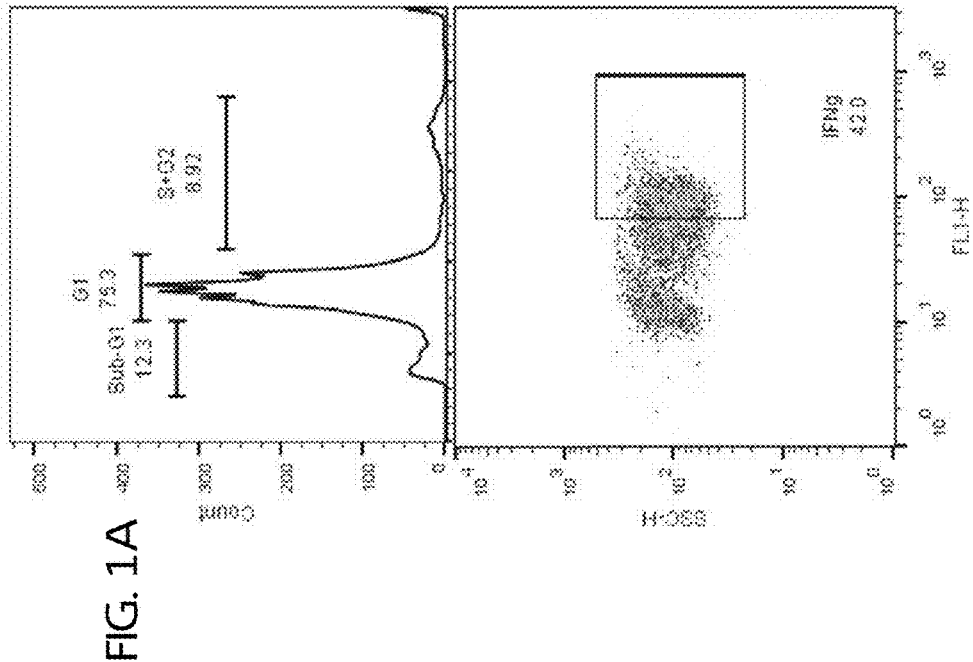

FIGS. 1A and 1B show the effects of a null control treatment on healthy PBMCS (FIG. 1A) and the effect of heat-treated whole blood on PBMCS (FIG. 1A), respectively, both with no added antigens/epitopes, with the top panels showing the cell cycle distribution of treated cells and the bottom panels showing the expression of gamma-interferon (IFNg) in treated cells. The experiment shows that heat-treated whole blood induced apoptosis in the PBMCs and reduced the number of cells expressing the proinflammatory cytokine gamma-interferon.

Figures 2A, 2B:
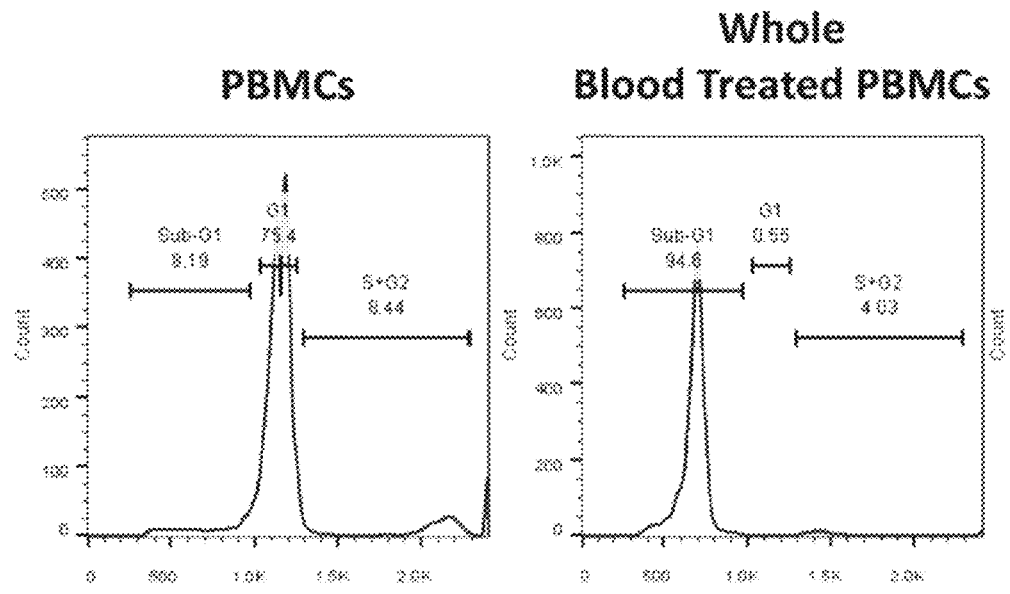
FIG. 2A shows the cell cycle distribution of cells in healthy PBMCs (control case).
FIG. 2B shows the cell cycle distribution of PBMCs treated with whole blood (not heat-treated).
Figures 2C, 2D:
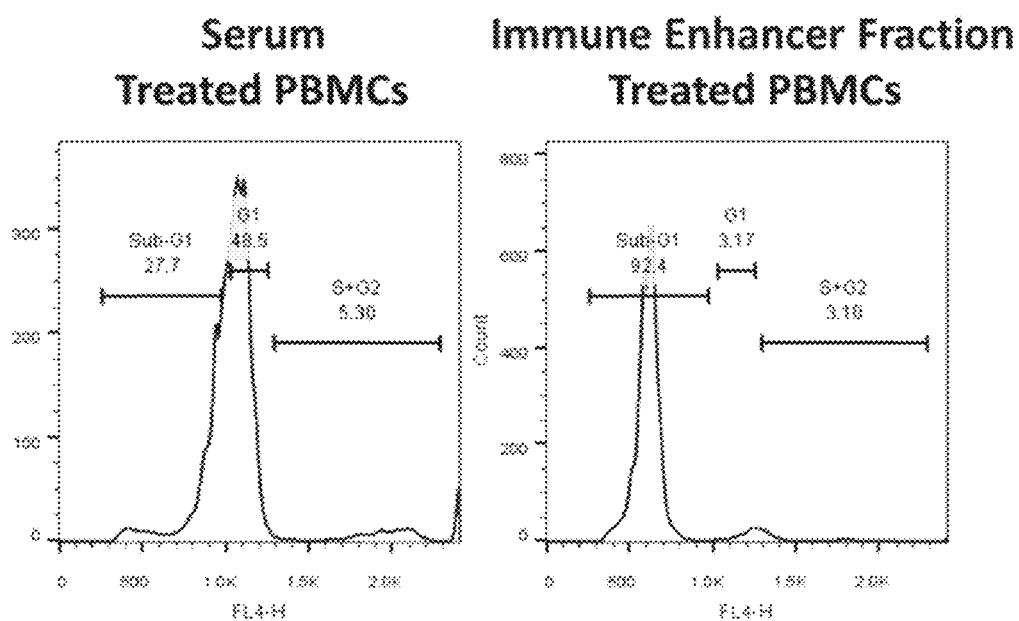
FIG. 2C shows the cell cycle distribution of PBMCs treated with serum.
FIG. 2D shows the cell cycle distribution of PBMCs treated with a heat-treated red blood cell (RBC) density gradient fraction (referred to as the "immune enhancer fraction;" "RBC;" and "IE" herein).

FIG. 2A shows the cell cycle distribution of cells in healthy PBMCs (control case). FIG. 2B shows the cell cycle distribution of PBMCs treated with heat treated whole blood. FIG. 2C shows the cell cycle distribution of PBMCs treated with heat treated serum. FIG. 2D shows the cell cycle distribution of PBMCs treated with a heat-treated red blood cell fraction (referred to as the "immune enhancer fraction;" "RBC;" and "IE" herein).

Figure 3A:
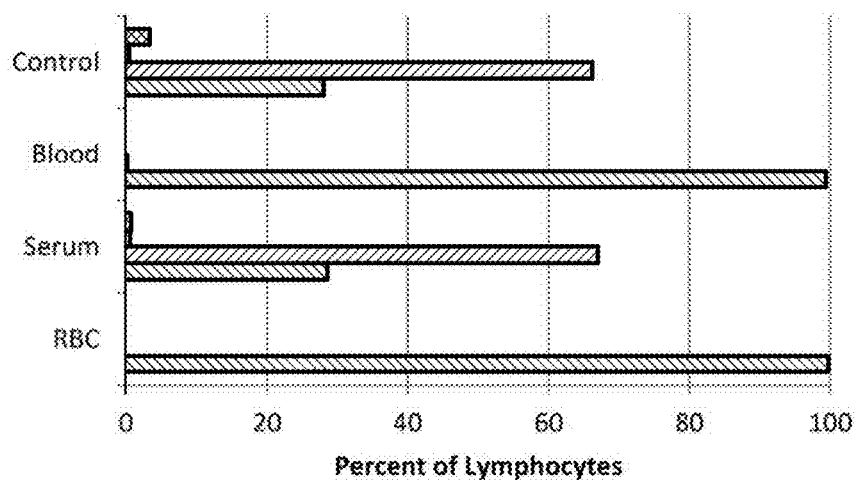
FIGS. 3A and 3B show cell cycle distribution of PBMCs treated with control and various heat-treated blood fractions for allogeneic blood (FIG. 3A) and autologous blood (FIG. 3B) indicating that that the apoptosis-inducing activity of whole blood is predominantly present in the RBC fraction, and is independent of the donor source.
Figure 3B:
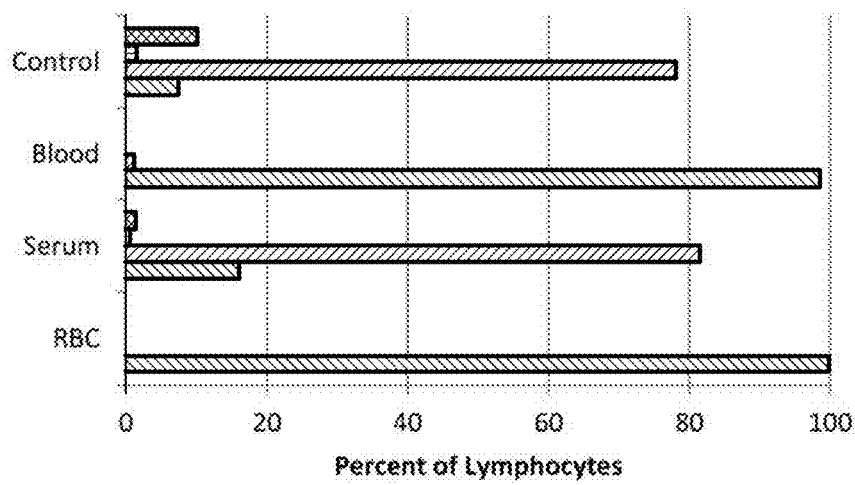

FIGS. 3A and 3B show cell cycle distribution of PBMCs treated with control and various heat-treated blood fractions for allogeneic blood (FIG. 3A) and autologous blood (FIG. 3B) indicating that that the apoptosis-inducing activity of whole blood is predominantly present in the RBC fraction and independent of donor source. Heat-treated IE showed essentially the same extent of apoptosis induction as heat-treated whole blood. The heat-treated serum fraction decreased cell proliferation but did not increase apoptosis. The IE dose was 50 μL.

FIGS. 4A-C show the effect of control (FIG. 4A), recombinant HLA-B protein (rHLA-B; FIG. 4B), and recombinant HLA-G protein (rHLA-G; FIG. 4C) on the cell cycle distribution of PBMCs, indicating apoptosis-inducing activity of the rHLA-G and rHLA-B proteins on the PBMCs.

Figure 5A:
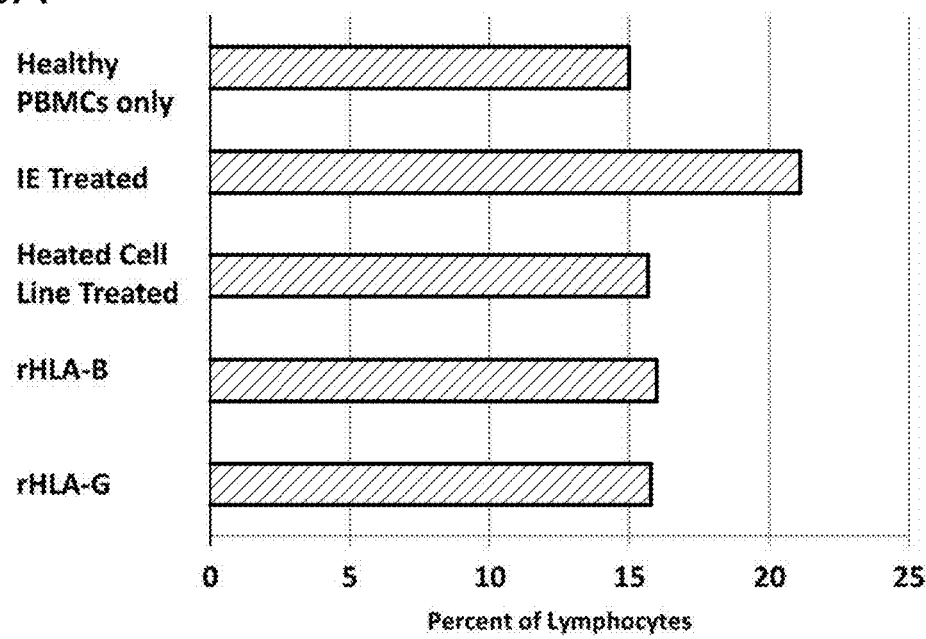
FIGS. 5A and 5B show the effect of various treatment on the percent of PBMCs in the sub-G1 phase (FIG. 5A) and the S+G2 phase (FIG. 5B).
Figure 5B:
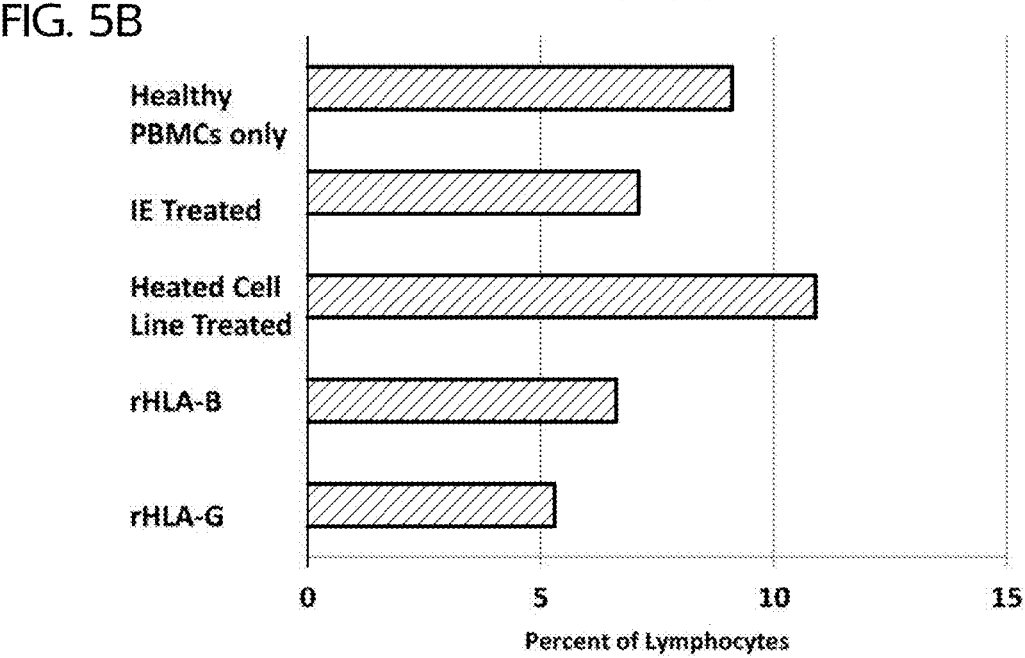

FIGS. 5A and 5B show the effect of various treatment on the percent of PBMCs in the sub-G1 phase (FIG. 5A) and the S+G2 phase (FIG. 5B). The heat-treated cell-line was a HeLa cell line. IE increased apoptosis and decreased proliferation of the lymphocytes (PBMCs). Recombinant HLA proteins (65 ng/mL) gave only minor induction of apoptosis, but decreased proliferation. The heat-treated HeLa cells did not mimic apoptosis induction and, in fact, induced higher proliferation. The IE dose was 5 μL. The lower dose induced less apoptosis compared to the 50 μL dose.

FIGS. 6A and 6B show the effect of various blocking factors on the ability of the immune enhancer (heat-treated RBC density gradient fraction) to affect the percentage of PBMCs in the sub-G1 phase (FIG. 6A) and the S+G2 phase (FIG. 6B). Anti-HLA-I and FasL blocking antibodies do not reverse IE-induced apoptosis. Anti-HLA-I antibody itself induces an increase in apoptosis independent of IE. Annexin V (which blocks phosphatidyl serine) shows no effect on apoptosis, but reduces proliferation in both control and IE treated groups.

Figure 7:
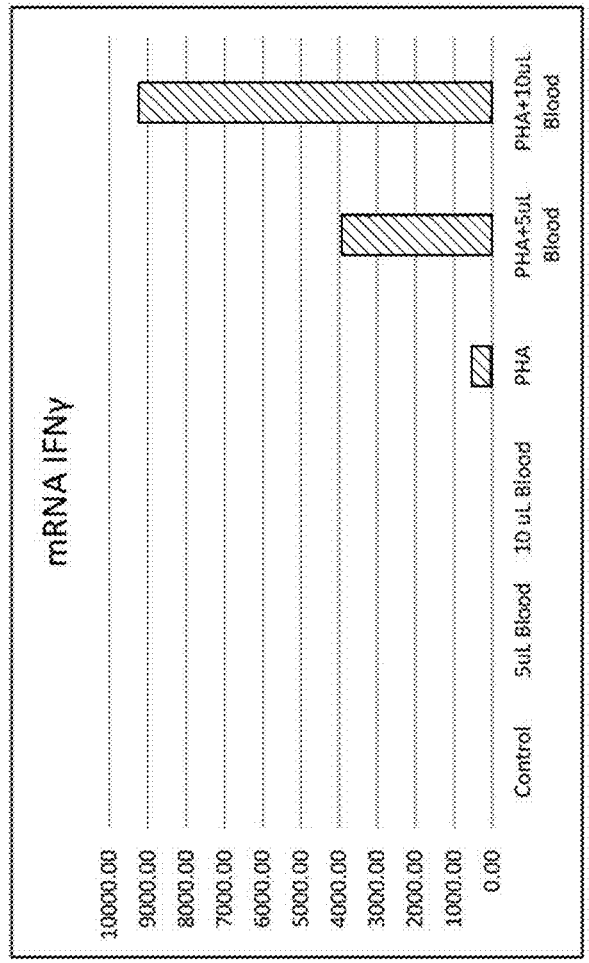
FIG. 7 shows the effect of different doses of IE on the ability of phytohemagglutinin (PHA) to induce gamma-interferon (IFNγ) expression in PBMCs, as measured by mRNA detection.

FIG. 7 shows the effect of different doses of IE on the ability of phytohemagglutinin (PHA) to induce gamma-interferon (IFNγ) expression in PBMCs, as measured by mRNA detection. IE stimulated the immune response to PHA in a dose-dependent manner.

Figures 8A, 8B, 8C:
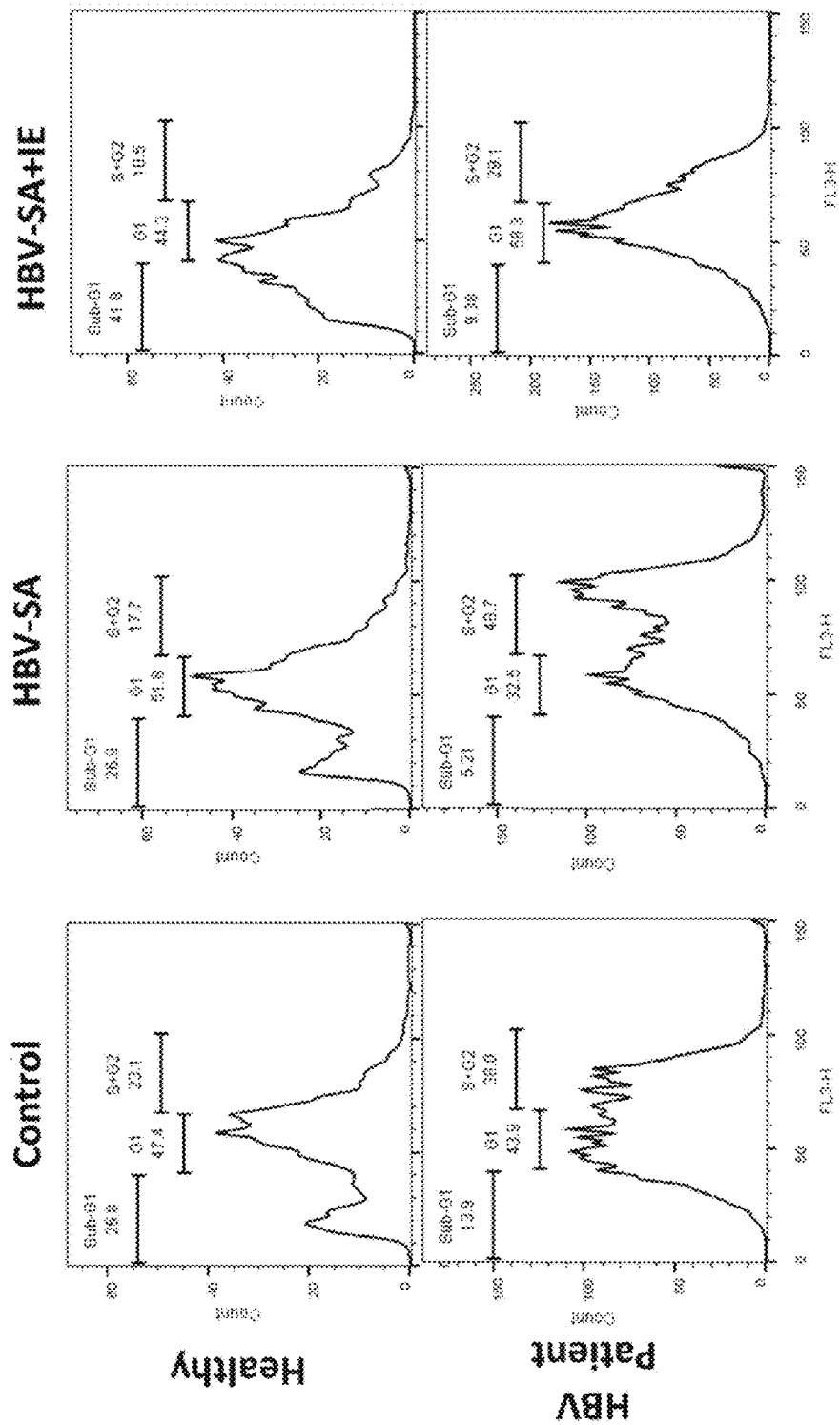
FIGS. 8A-8C show the effects on cell cycle distribution of control (FIG. 8A), Hepatitis B virus S-antigen ("HBV-SA.
Figures 9A, 9B, 9C, 9D:
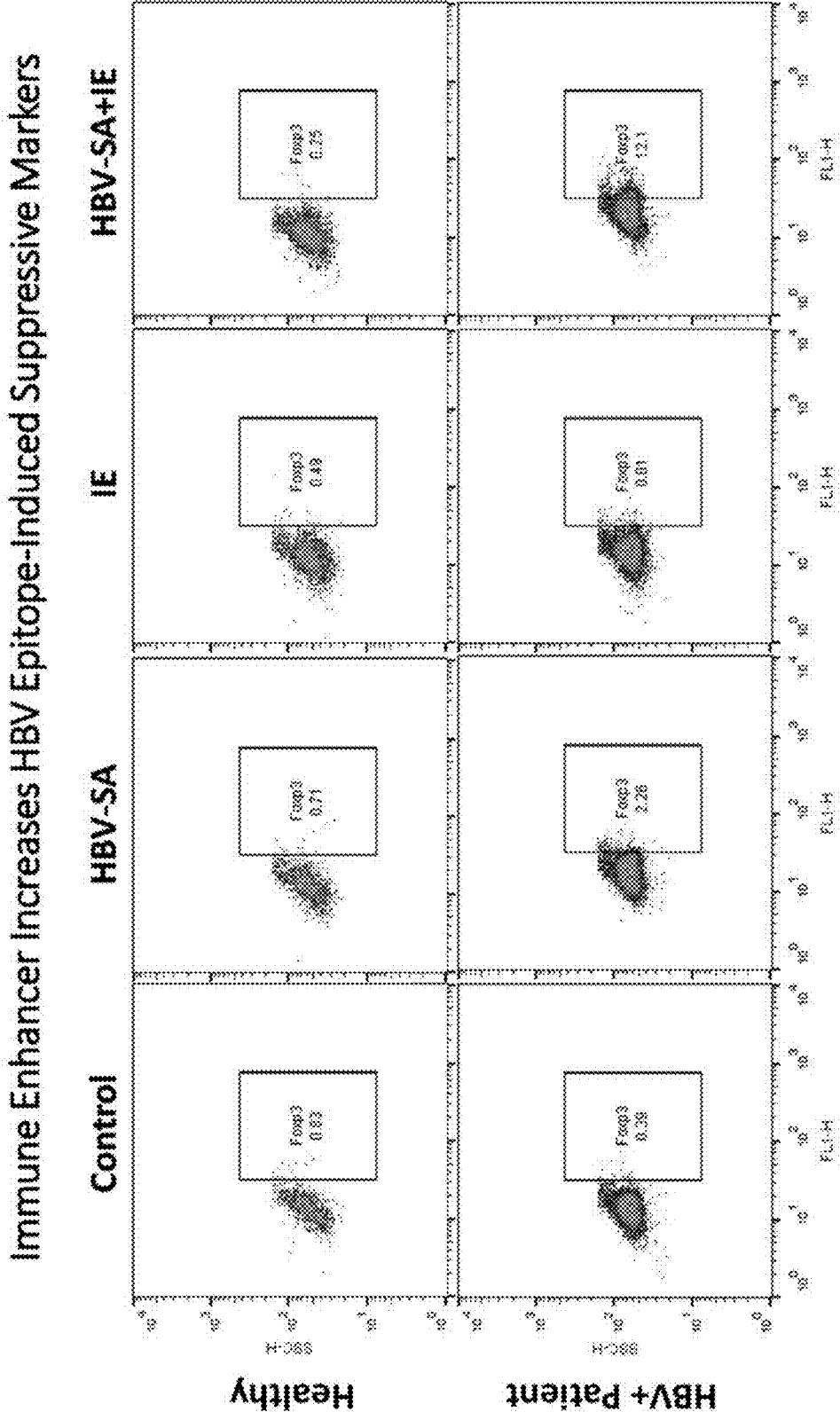
FIGS. 9A-D show the effect of control (FIG. 9A), HBV-SA alone (FIG. 9B), IE alone (FIG. 9C), and HBV-SA plus IE (FIG. 9D) on the expression of the Foxp3 immune suppression marker in PBMCs from healthy human subjects (top panels) and HBV patients (bottom panels).

FIGS. 8A-8C show the effects on cell cycle distribution of control (FIG. 8A), hepatitis B virus S-antigen ("HBV-SA;" FIG. 8B) alone, and HBV-A plus IE (FIG. 8C) on PBMCs from healthy human subjects (top panels) and HBV patients (bottom panels). For the healthy control PBMCs (non-HBV-infected subject), the addition of HBV-SA alone had little/no effect while the addition of HBV-SA plus IE had a pronounced pro-apoptotic effect. For PBMCs from HBV-infected subjects, the addition of HBV-SA only shifted the cells toward proliferation (versus control) while the addition of HBV-SA plus IE reduced proliferation versus both control and HBV-SA alone.

FIGS. 9A-D show the effect of control (FIG. 9A), HBV-SA alone (FIG. 9B), IE alone (FIG. 9C), and HBV-SA plus IE (FIG. 9D) on the expression of the Foxp3 immune suppression (Treg) marker in PBMCs from healthy human subjects (top panels) and HBV patients (bottom panels).

Figure 10:
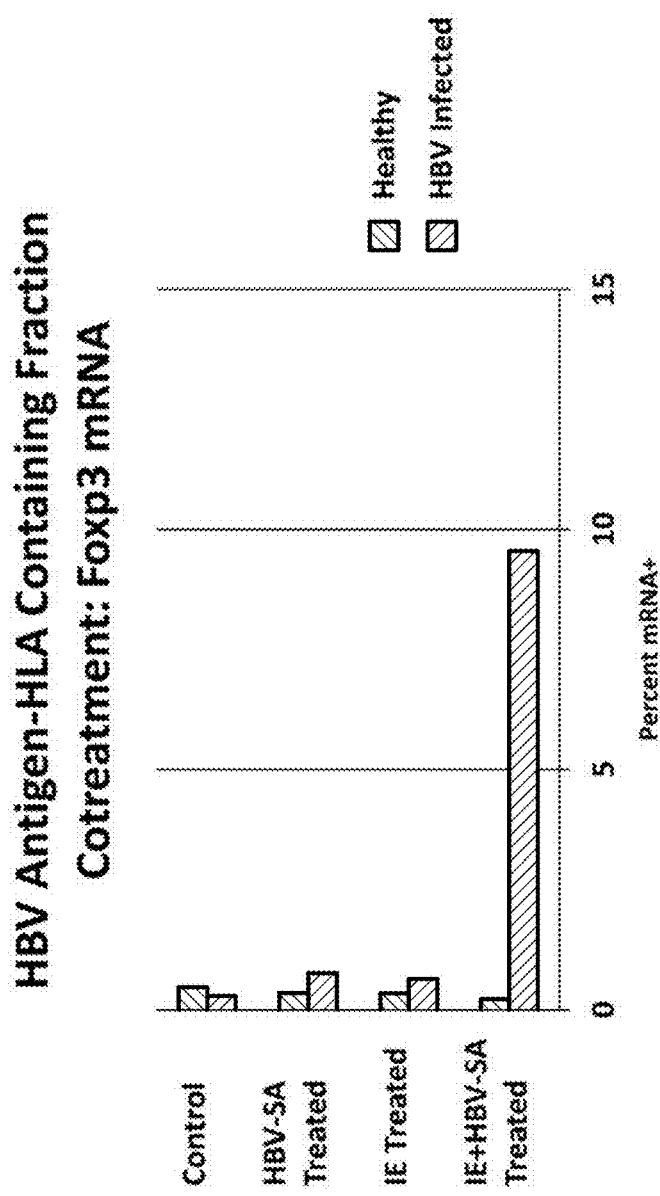
FIG. 10 shows the percent increase in Foxp3 mRNA for control and different treatments in the experiment shown in FIGS. 9A-D.

FIG. 10 shows the percent increase in Foxp3 mRNA for control and different treatments in the experiment shown in FIGS. 9A-D. Low-dose IE (5 μL) increased expression of anti-inflammatory marker Foxp3 by cells from an antigen responsive patient in the presence of the antigen. IE alone did not increase expression of Foxp3. Foxp3 expression correlated with antigen-specific suppression in the presence of low-dose IE, in contrast to the general suppression of apoptosis seen with high-dose IE.

Figures 11A, 11B:
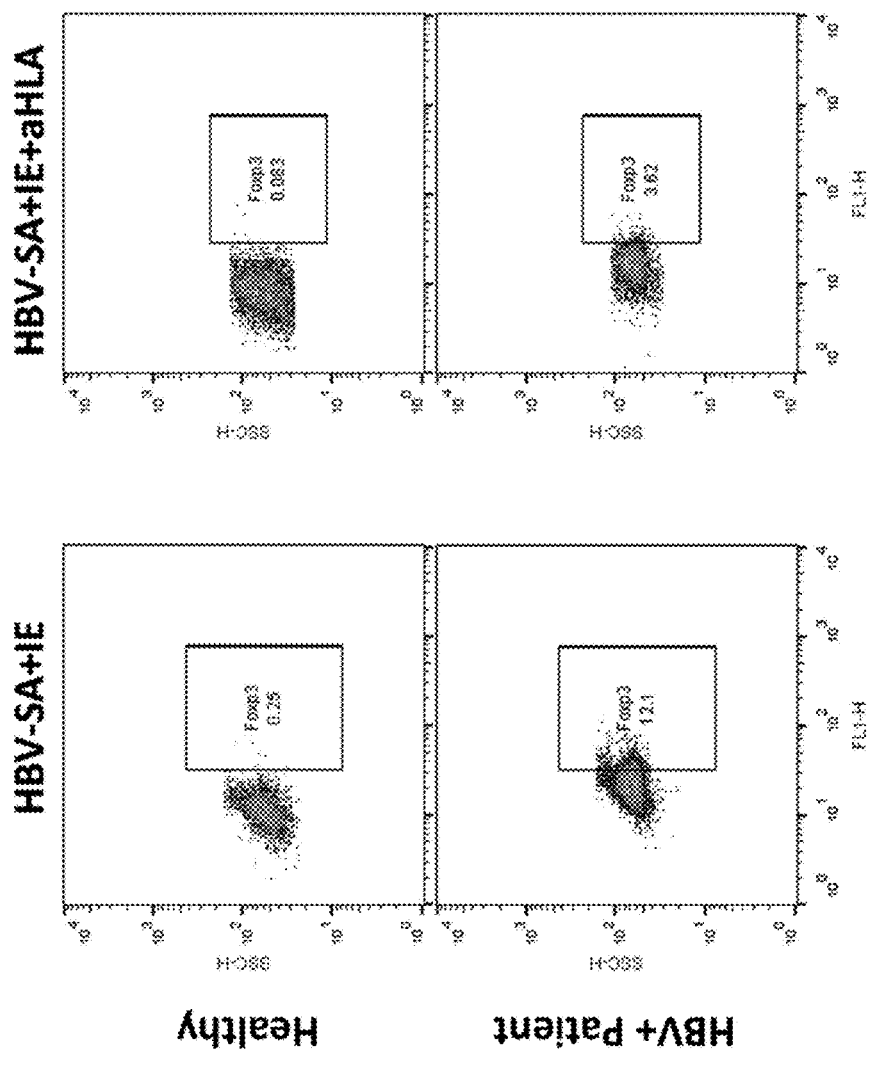
FIGS. 11A and 11B show the effect of HBV-SA plus IE (FIG. 11A) and HBV-SA plus IE plus anti-HLA class I antibody (aHLA) on the expression of the Foxp3 immune suppression marker in PBMCs from healthy human subjects (top panels) and HBV patients (bottom panels).
Figures 12A, 12B, 12C, 12D:
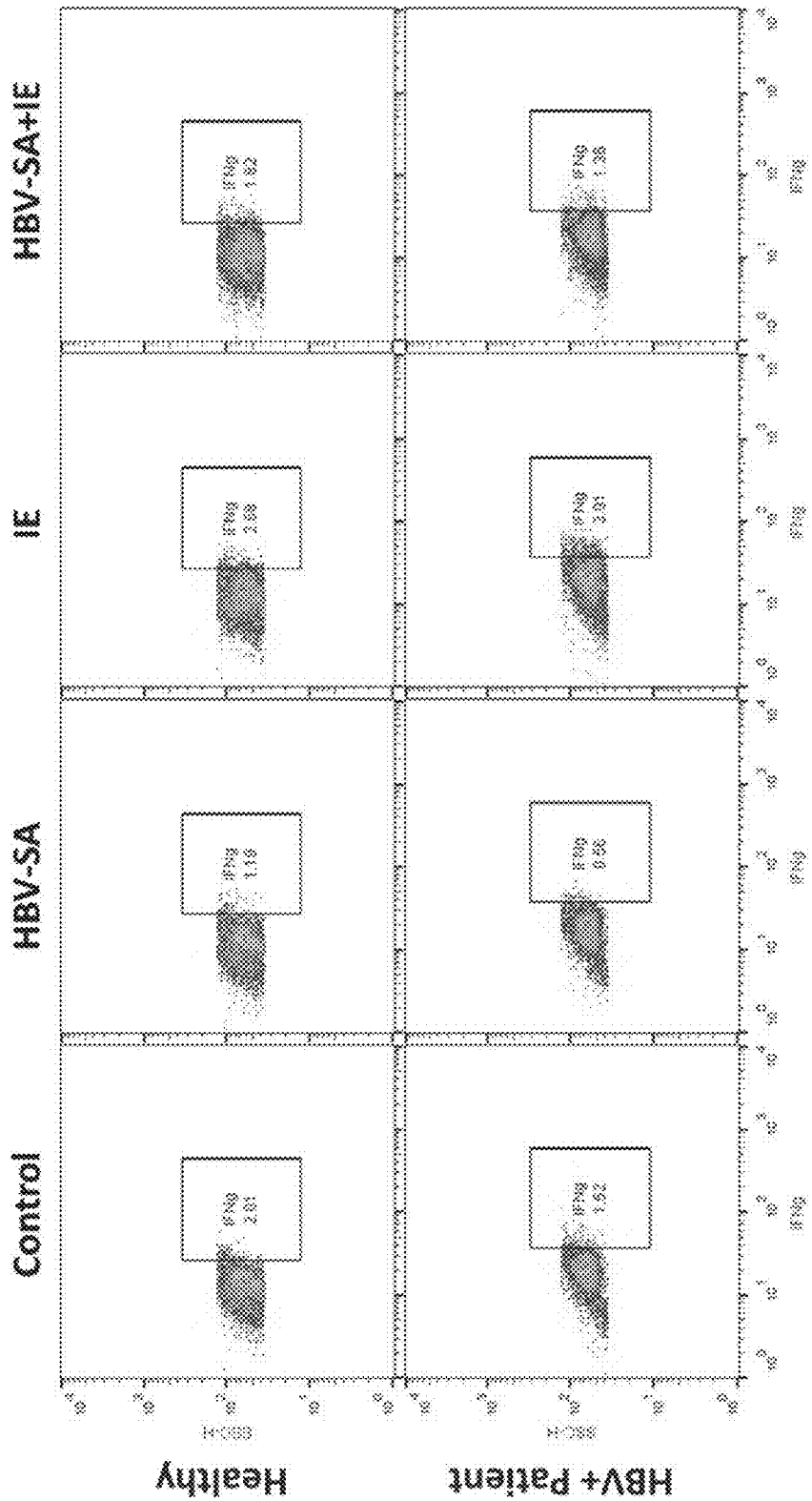
FIGS. 12A-D show the effect of control (FIG. 12A), HBV-SA alone (FIG. 12B), IE alone (FIG. 12C), and HBV-SA plus IE (FIG. 12D) on the expression of gamma interferon in PBMCs from healthy human subjects (top panels) and HBV patients (bottom panels).

FIGS. 11A and 11B show the effect of HBV-SA plus IE (FIG. 11A) and HBV-SA plus IE plus anti-HLA class I antibody (aHLA) on the expression of the Foxp3 immune suppression marker in PBMCs from healthy human subjects (top panels) and HBV patients (bottom panels). The experiment shows that an anti-HLA class I antibody partially blocks the induction of the Foxp3 marker by HBV-SA plus IE in both healthy PMBCs and PBMCs from HBV-infected subjects.

FIGS. 12A-D show the effect of control (FIG. 12A), HBV-SA alone (FIG. 12B), IE alone (FIG. 12C), and HBV-SA plus IE (FIG. 12D) on the expression of gamma interferon in PBMCs from healthy human subjects (top panels) and HBV patients (bottom panels).

FIGS. 13A and 13B show the effect of HBV-SA plus IE (FIG. 13A) and HBV-SA plus IE plus anti-HLA class I antibody (aHLA) on the expression of gamma interferon (IFNg) in PBMCs from healthy human subjects (top panels) and HBV patients (bottom panels).

In still another experiment, it was shown that low-dose IE induced gamma-interferon release from PBMCs, while medium-dose IE shifted the response toward IL-10 (an immunosuppressive cytokine) production and high-dose IE further shifted the response toward inducing apoptosis.

Figure 14:
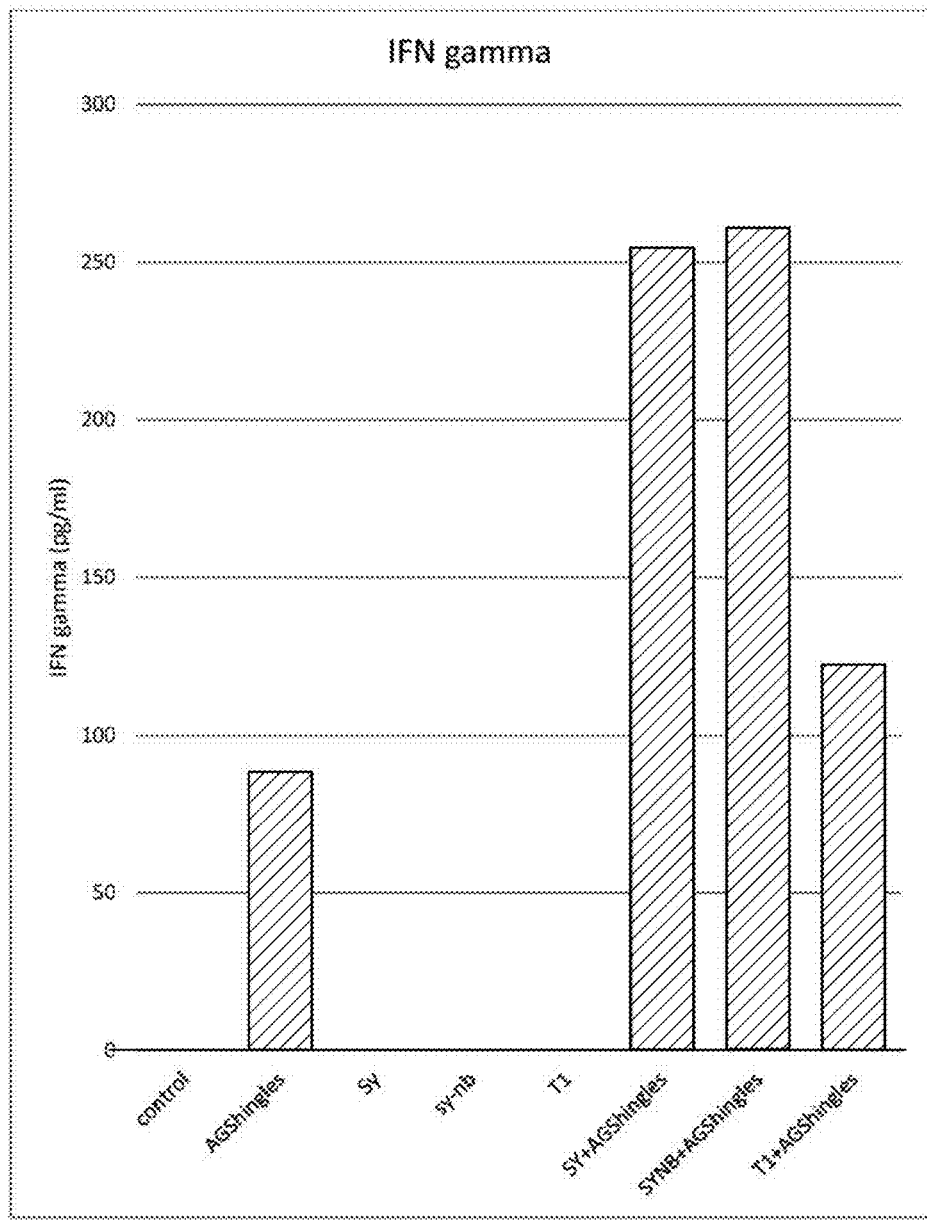
FIG. 14 shows the antigen-dependent, immune stimulation-enhancing activity of human alpha-synuclein protein (as measured by IFN-gamma release) during antigen challenge of whole blood from a subject recently immunized with the subject antigen.

FIG. 14 shows the immune stimulation-enhancing activity of human alpha-synuclein protein (as measured by IFN-gamma release) for antigen challenge of whole blood from a subject recently immunized with the subject antigen. Whole blood for testing was obtained from a human subject recently immunized (approximately one week) with an approved shingles vaccine (i.e., immunized against Varicella zoster (chickenpox) virus antigens). Fresh whole blood aliquots were mixed with control and test protein/antigen compositions, and incubated at 37° C. for 24 hours. IFN-gamma release was then evaluated by ELISA assay. As shown in FIG. 14, the following controls and tests were performed: control (whole blood only; no added antigen or proteins); AGShingles (whole blood plus two antigens (Varicella zoster virus ORF 26 recombinant protein and Varicella zoster virus ORF 9 recombinant protein) present in the shingles vaccine the subject received); sy (whole blood plus boiled alpha-synuclein protein); synb (whole blood plus alpha-synuclein protein not boiled); T1 (whole blood plus heat-treated whole blood); SY+AGShingles (whole blood plus boiled alpha-synuclein and AGShingles); SYNB+AG-Shingles (whole blood plus not boiled alpha-synuclein and AGShingles); and T1+AGShingles (whole blood plus T1 and AGShingles). IFN gamma release in the experiment is indicative of effector T-cell stimulation in the whole blood. As shown, control, sy, synb and T1 alone (i.e., all without added Varicella zoster virus antigen) did not cause IFN gamma release. The Varicella zoster virus antigens alone caused IFN release (approximately 87 pg/ml). T1 plus the Varicella zoster virus antigens caused a moderately, further increased release of TFN gamma (approximately 122 pg/ml). In contrast, both sy plus the Varicella zoster virus antigens and synb plus the Varicella zoster virus antigens caused a dramatic increase in IFN gamma release (in each case to above 250 pg/ml). Thus, alpha-synuclein acts a potent enhancer of immune response against antigen.

The recombinant human HLA-B used in the experiments, which may also be used in the various embodiments, was cat# RPC140684-50 μg from Biomatik USA, LLC (Wilmington, Del., USA). The amino acid sequence of said HLA-B is shown in SEQ ID NO: 1.

The recombinant human HLA-G used in the experiments, which may also be used in the various embodiments, was cat# RPC140674-50 μg from Biomatik USA, LLC (Wilmington, Del., USA). The amino acid sequence of said HLA-G is shown in SEQ ID NO: 2.

The recombinant human alpha-synuclein used in the experiments, which may also be used in the various embodiments, was cat # PRO-393 from ProSpec-Tany TechnoGene Ltd. ("ProspecBio;" East Brunswick, N.J., USA). The amino acid sequence of said human alpha-synuclein is shown in SEQ ID NO: 3. Varicella Zoster Virus ORF 26 recombinant protein used in the experiments was ProspecBio cat# Pro-233 and Varicella Zoster Virus ORF 9 recombinant protein used in the experiments was ProspecBio cat# Pro-232.

The ability of red blood cells to augment immune responses has been previously described, especially with respect to immunosuppression arising from red blood cell transfusions. Speculation for the elements that might be responsible on the surface of red blood cells for this effect have led to studies of LFA-3, a protein that is highly enriched in red blood cells. With regard to immune processes, LFA-3 is a ligand on antigen-presenting cells (APCs) that interacts with the CD2 receptor on CD4+ cells and is thought to be a co-activator that works in conjunction with the interaction between HLAs and TCRs on T-cells. It should be pointed out that the LFA-3 in a blood preparation is in the context of being present on APCs and not as a free ligand. Nevertheless, soluble LFA-3 was tested (in the same manner as alpha-synuclein) for an ability to induce an antigen-specification stimulation/modulation. The results showed that the presence of LFA-3 had no effects on immune responses in PBMCs exposed to antigen. Thus, it was determined that, in contrast to alpha-synuclein, LFA-3 in solution does not have antigen-specific immune-modulating activity.

Without limitation, the invention also provides the following enumerated embodiments.

Embodiment 1

An immunomodulatory pharmaceutical composition including a mixture of:
  (i) a first component including
    (a) at least partially purified HLA protein or fragments thereof, such as mammalian, for example human,
    (b) whole blood, such as mammalian, for example human, or a cellular fraction thereof, such as a density gradient fraction/layer thereof, such as but not limited to a white blood cell and/or red blood cell (erythrocyte) and/or platelet fraction/layer thereof, or a cell membrane fraction/preparation of any of the foregoing or a protein extract of any of the foregoing, and/or
    (c) alpha-synuclein protein, such as mammalian alpha-synuclein protein, such as human alpha-synuclein protein, or fragments thereof; and
  (ii) at least one preselected antigen or immunogen, such as at least one preselected peptide antigen, at least one preselected protein antigen, at least one preselected carbohydrate antigen, at least one preselected lipid antigen, and/or at least one preselected glycolipid antigen. For example, the at least one preselected antigen or immunogen may be other than an HLA protein or fragment thereof and/or other than a synuclein protein or fragment thereof, such as other than a mammalian alpha-synuclein protein or fragment thereof.

Embodiment 2

The immunomodulatory pharmaceutical composition of embodiment 1, in which the first component, such as at least partially purified HLA protein, is heat-treated, for example, heat-treated at or above 100° C. for at least 1 or 2 or 3 or 4 or 5 minutes.

Embodiment 3

The immunomodulatory pharmaceutical composition of embodiment 1, in which the at least partially purified HLA protein is at least substantially denatured.

Embodiment 4

The immunomodulatory pharmaceutical composition of any one of the preceding embodiments, in which the first component includes at least partially purified HLA protein is recombinant, such as full length or partial length recombinant protein.

Embodiment 5

The immunomodulatory pharmaceutical composition of embodiments 1-3, in which the at least partially purified HLA protein is derived from a tissue source.

Embodiment 6

The immunomodulatory pharmaceutical composition of embodiment 5, in which the tissue source includes blood cells.

Embodiment 7

The immunomodulatory pharmaceutical composition of embodiment 5, in which the tissue source at least substantially or at least predominantly includes red blood cells.

Embodiment 8

The immunomodulatory pharmaceutical composition of any one of the preceding embodiments, in which the at least one preselected peptide antigen includes a synthetic peptide. The peptide may, for example, be 5-20 amino acids in length or any subrange thereof or number of amino acids therein.

Embodiment 9

The immunomodulatory pharmaceutical composition of any one of the preceding embodiments, in which the at least one preselected antigen includes a self-antigen.

Embodiment 10

The immunomodulatory pharmaceutical composition of embodiment 9, in which the self-antigen is associated with an autoimmune disease.

Embodiment 11

The immunomodulatory pharmaceutical composition of any one of embodiments 1-8, in which the at least one preselected antigen is a cancer-associated antigen or an antigen preferentially expressed on cancer cells versus normal cells.

Embodiment 12

The immunomodulatory pharmaceutical composition of any one of the preceding embodiments, in which the at least partially purified HLA protein includes at least partially purified mammalian HLA protein.

Embodiment 13

The immunomodulatory pharmaceutical composition of embodiment 12, in which the at least partially purified mammalian HLA protein includes at least partially purified human HLA protein.

Embodiment 14

The immunomodulatory pharmaceutical composition of any one of the preceding embodiments, in which the composition is in a form selected from the group consisting of a liquid form and an at least substantially dry form, such as a powder form or tableted form. A dry form may, for example, be obtained by lyophilizing or otherwise drying a liquid mixture of the components.

Embodiment 15

The immunomodulatory pharmaceutical composition of embodiment 14, in which the composition is a parenteral composition.

Embodiment 16

The immunomodulatory pharmaceutical composition of embodiment 15, in which the composition is an injectable composition.

Embodiment 17

The immunomodulatory pharmaceutical composition of any one of the preceding embodiments, in which the at least partially purified HLA protein includes one or more of HLA-A, HLA-B, HLA-C and HLA-G protein.

Embodiment 18

The immunomodulatory pharmaceutical composition of embodiment 17, in which the at least partially purified HLA protein includes HLA-G protein.

Embodiment 19

The immunomodulatory pharmaceutical composition of any one of the preceding embodiments, in which the at least partially purified HLA protein includes HLA Class II protein.

Embodiment 20

A method for manufacturing an immunomodulatory pharmaceutical composition including the steps of:
providing a first component including
(a) at least partially purified HLA protein or fragments thereof, such as mammalian, for example human, (b) whole blood, such as mammalian, for example human, or a cellular fraction thereof, such as a density gradient fraction thereof, such as but not limited to a white blood cell and/or red blood cell (erythrocytes) and/or platelet fraction/layer thereof, or a cell membrane fraction/preparation of any of the foregoing or a protein extract of any of the foregoing, and/or (c) alpha-synuclein protein, such as mammalian alpha-synuclein protein, such as human alpha-synuclein protein, or fragments thereof; and providing a second component including at least one preselected antigen or immunogen, such as at least one preselected peptide antigen, at least one preselected protein antigen, at least one preselected carbohydrate antigen, at least one preselected lipid antigen, and/or at least one preselected glycolipid antigen; and mixing the first component and the second component, for example, under aqueous conditions.

Embodiment 21

The method of embodiment 20, in which the at least partially purified HLA protein is provided and the method further includes the step of:

heat-treating the at least partially purified HLA protein before the mixing step.

Embodiment 22

The method of embodiment 20, in which at least partially purified HLA protein is provided and the method further includes the step of:

denaturing the at least partially purified HLA protein before the mixing step.

Embodiment 23

The method of embodiment 20, further including the step of:

heat-treating the composition after the mixing step.

Embodiment 24

The method of embodiment 20, in which the providing step includes providing said fragments, and the mixing step includes mixing said fragments with said second component.

Embodiment 25

The method of any one of embodiments 20-24, in which the at least partially purified HLA protein includes recombinant HLA protein.

Embodiment 26

The method of any one of embodiments 20-24, in which the at least partially purified HLA protein is derived from a tissue source.

Embodiment 27

The method of embodiment 26, in which the tissue source includes blood cells.

Embodiment 28

The method of embodiment 27, in which the tissue source at least substantially includes red blood cells.

Embodiment 29

The method of any one of embodiments 20-28, in which the at least one preselected antigen includes a synthetic peptide.

Embodiment 30

The method of any one of embodiments 20-29, in which the at least one preselected antigen includes a self-antigen.

Embodiment 31

The method of embodiment 30, in which the self-antigen is associated with an autoimmune disease.

Embodiment 32

The method of any one of embodiments 20-29, in which the at least one preselected antigen, which may, for example, be or include one or more synthetic peptides, includes a cancer-associated antigen/epitope or an antigen/epitope preferentially expressed on cancer cells versus normal cells.

Embodiment 33

The method of any one of embodiments 20-29, in which the at least one preselected peptide antigen includes an antigen of a virus or cellular microorganism, such as a pathogenic virus or cellular microorganism, for example for a mammal such as human. Without limitation, the at least one preselected antigen of a pathogenic virus may, for example, be or include an antigen of or associated with Hepatitis B virus, Hepatitis C virus, Influenza virus, HIV-1 or HIV-2. For example, the virus may be Hepatitis B and the at least one preselected antigen may be one or more of HBsAg (surface antigen, S-protein) such as SEQ ID NO: 37 (adw serotype) and/or SEQ ID NO: 38 (adr serotype), HB pre-S1 protein (SEQ ID NO: 39), HB pre-S2 protein (SEQ ID NO: 40), HBeAg (HepB envelope antigen; e.g., SEQ ID NO: 41), and HBcAg (HepB core antigen; e.g. SEQ ID NO: 42). Without limitation the at least one preselected antigen of a pathogenic cellular microorganism may, for example, be or include an antigen of or associated with a pathogenic bacteria, fungi, or amoeba.

Embodiment 34

The method of any one of embodiments 20-33, in which the at least partially purified HLA protein includes one or more of HLA-A, HLA-B, HLA-C and HLA-G protein.

Embodiment 35

The method of embodiment 34, in which the at least partially purified HLA protein includes HLA-G.

Embodiment 36

The method of any one of embodiments 20-35, in which the at least partially purified HLA protein includes HLA Class II protein.

Embodiment 37

A method for modulating the immune response in a mammal to at least one preselected antigen or immunogen including administering to the mammal the immunomodulatory pharmaceutical composition of any one of embodiments 1-19. Said administration may be parenteral or non-parenteral. Said administration may, for example be via ingestion. Where administration is via ingestion, an antacid may be co-administered. The composition may, for example, be an enteric composition for ingestion. Administration may, for example, be via injection, such as intravenous injection, intra-thymic injection or injection into a lymph node of a subject.

Embodiment 38

The method of embodiment 36, in which said administration is parenteral.

Embodiment 39

The method of embodiment 36, in which said administration is via injection.

Embodiment 40

The method of any one of embodiments 36-38, in which the mammal is a human.

Embodiment 41

The method of any one of embodiments 36-39, in which the resultant modulation of the immune response is immunosuppressive (pro-regulatory cell response) with respect to the at least one preselected antigen or immunogen. Thus, alpha-synuclein may be used as a pro-regulatory (-immunosuppressive) response adjuvant.

Embodiment 42

The method of any one of embodiments 36-39, in which the resultant modulation of the immune response is immunostimulatory (pro-effector cell response) with respect to the at least one preselected antigen or immunogen. Thus, alpha-synuclein may be used as a pro-effector response adjuvant.

Embodiment 43

Use of a composition according to any one of embodiments 1-19 for modulating the immune response in a mammal, such as a human, to the at least one preselected antigen or immunogen.

Embodiment 44

The use of embodiment 43, in which the modulation of the immune response is immunosuppressive with respect to the at least one preselected antigen or immunogen.

Embodiment 45

The use of embodiment 43, in which the modulation of the immune response is immunostimulatory with respect to the at least one preselected antigen or immunogen.

Embodiment 46

Use of alpha-synuclein protein, such as mammalian alpha-synuclein protein, such as human alpha-synuclein protein, or fragments thereof, as an immune stimulator or adjuvant in conjunction with a vaccination (use of a vaccine), for example, in a mammal such as but not limited to a human, such as, in conjunction with vaccination against a pathogen or a cancer antigen or in conjunction with use of a cancer vaccine.

Embodiment 47

Use of alpha-synuclein protein, such as mammalian alpha-synuclein protein, such as human alpha-synuclein protein, or fragments thereof, as an immunization adjuvant or vaccine adjuvant, for example, in a mammal such as but not limited to a human.

Embodiment 48

A method for enhancing the immune response to an immunization with an immunogen in a subject such as a mammal, such as but not limited to a human, comprising the step of: coadministering to the subject alpha-synuclein protein, such as mammalian alpha-synuclein protein, such as human alpha-synuclein protein, or fragments thereof, with the immunogen.

Embodiment 49

A method for enhancing the immune response of a mammalian subject, such as but not limited to a human, having a malignancy, such as a blood cancer/malignancy or a solid tumor, to said malignancy and/or a method for treating such a malignancy in a such a subject, comprising the step of: administering to the subject alpha-synuclein protein, such as mammalian alpha-synuclein protein, such as human alpha-synuclein protein, or fragments thereof. Said administration may be with or without at least one preselected antigen. Said blood cancer/malignancy may, for example, be Myelodysplastic syndrome (MDS), a leukemia, such as Acute lymphoblastic leukemia (ALL) or Acute myeloid leukemia (AML), or a lymphoma, such as a Hodgkin lymphoma, non-Hodgkin lymphoma or mantle cell lymphoma. Said malignancy may, for example, be a liver cancer such as hepatocellular carcinoma (HCC) or cholangiocarcinoma, pancreatic cancer, breast cancer, prostate cancer, kidney cancer, melanoma, myeloma, glioblastoma, ovarian cancer, testicular cancer, bone cancer such as osteosarcoma, or lung cancer such as non-small cell lung cancer or small cell lung cancer.

Embodiment 50

Use of alpha-synuclein protein, such as mammalian alpha-synuclein protein, such as human alpha-synuclein protein, or fragments thereof, in the treatment of a malignancy/cancer, such as a blood cancer or a solid tumor, in a mammal such as but not limited to a human. Said administration may be with or without at least one preselected antigen. Said blood cancer/malignancy may, for example, be Myelodysplastic syndrome (MDS), a leukemia, such as ALL or AML, or a lymphoma, such as a Hodgkin lymphoma, non-Hodgkin lymphoma or mantle cell lymphoma. Said malignancy may, for example, be a liver cancer such as hepatocellular carcinoma (HCC) or cholangiocarcinoma, pancreatic cancer, breast cancer, prostate cancer, kidney cancer, melanoma, myeloma, glioblastoma, ovarian cancer,

Embodiment 51

Use of alpha-synuclein protein, such as mammalian alpha-synuclein protein, such as human alpha-synuclein protein, or fragments thereof, in the preparation of a medicament for the treatment of a malignancy, such as a blood cancer or a solid tumor, in a mammal such as but not limited to a human. Said medicament may include or exclude at least one preselected antigen as described herein. Said blood cancer/malignancy may, for example, be Myelodysplastic syndrome (MDS), a leukemia, such as ALL or AML, or a lymphoma, such as a Hodgkin lymphoma, non-Hodgkin lymphoma or mantle cell lymphoma. Said malignancy may, for example, be a liver cancer such as hepatocellular carcinoma (HCC) or cholangiocarcinoma, pancreatic cancer, breast cancer, prostate cancer, kidney cancer, melanoma, myeloma, glioblastoma, ovarian cancer, testicular cancer, bone cancer such as osteosarcoma, or lung cancer such as non-small cell lung cancer or small cell lung cancer.

Embodiment 52

A pharmaceutical composition for the treatment of a malignancy, such as a blood cancer or a solid tumor, in a mammal such as but not limited to a human, said composition comprising a therapeutically effective amount of alpha-synuclein protein, such as mammalian alpha-synuclein protein, such as human alpha-synuclein protein, or fragments thereof. The composition may further include one or more pharmaceutically acceptable excipients. Said blood cancer/malignancy may, for example, be Myelodysplastic syndrome (MDS), a leukemia, such as ALL or AML, or a lymphoma, such as a Hodgkin lymphoma, non-Hodgkin lymphoma or mantle cell lymphoma. Said malignancy may, for example, be a liver cancer such as hepatocellular carcinoma (HCC) or cholangiocarcinoma, pancreatic cancer, breast cancer, prostate cancer, kidney cancer, melanoma, myeloma, glioblastoma, ovarian cancer, testicular cancer, bone cancer such as osteosarcoma, or lung cancer such as non-small cell lung cancer or small cell lung cancer.

Embodiment 53

A method for enhancing the immune response of a mammalian subject, such as but not limited to a human, having an infectious disease, such as a microbial or viral infection, to said infectious disease, comprising the step of: administering to the subject alpha-synuclein protein, such as mammalian alpha-synuclein protein, such as human alpha-synuclein protein, or fragments thereof. Said administration may be with or without at least one preselected antigen as described herein.

Embodiment 54

Use of alpha-synuclein protein, such as mammalian alpha-synuclein protein, such as human alpha-synuclein protein, or fragments thereof, in the treatment of an infectious disease, such as a microbial or viral infection, in a mammal such as but not limited to a human. Said use may be in combination with or exclude at least one preselected antigen as described herein.

Embodiment 55

Use of alpha-synuclein protein, such as mammalian alpha-synuclein protein, such as human alpha-synuclein protein, or fragments thereof, in the preparation of a medicament for the treatment of an infectious disease, such as a microbial or viral infection, in a mammal such as but not limited to a human. Said medicament may include or exclude at least one preselected antigen as described herein.

Embodiment 56

A pharmaceutical composition for the treatment of an infectious disease, such as a microbial or viral infection, in a mammal such as but not limited to a human, said composition comprising a therapeutically effective amount of alpha-synuclein protein, such as mammalian alpha-synuclein protein, such as human alpha-synuclein protein, or fragments thereof. The composition may further include one or more pharmaceutically acceptable excipients. The composition may include or exclude at least one preselected antigen as described herein. In one example, the viral infection is Hepatitis B. In a related example, the viral infection is Hepatitis B and the composition includes at least one Hepatitis B protein or peptide antigen such as but not limited to one or more of HBsAg (surface antigen, S-protein) such as SEQ ID NO: 37 (adw serotype) and/or SEQ ID NO: 38 (adr serotype), HB pre-S1 protein (SEQ ID NO: 39), HB pre-S2 protein (SEQ ID NO: 40), HBeAg (HepB envelope antigen; e.g., SEQ ID NO: 41), and HBcAg (HepB core antigen; e.g. SEQ ID NO: 42).

Embodiment 57

An immunomodulatory pharmaceutical composition including, for example as or in a mixture:
(a) at least substantially pure alpha-synuclein protein or a fragment thereof and
(b) at least one preselected antigen, such as a peptide antigen, or immunogen, which antigen or immunogen is not a human or non-human mammalian alpha-synuclein protein or a fragment thereof.
In one variation, the at least one preselected antigen or at least one preselected immunogen does not comprise a synuclein protein and/or does not comprise a fragment of a synuclein protein.

Embodiment 58

The immunomodulatory pharmaceutical composition of embodiment 57, further including at least partially purified human or non-human mammalian HLA protein or fragments thereof, wherein the at least one preselected antigen or immunogen does not include human or non-human mammalian HLA protein or fragments thereof.

Embodiment 59

The immunomodulatory pharmaceutical composition of embodiment 57, wherein the composition does not include HLA protein or fragments thereof.

Embodiment 60

Any of composition embodiments 57-59, further including at least one pharmaceutically acceptable excipient.

Embodiment 61

A method for modulating the immune response in a mammal to at least one preselected antigen or immunogen including administering to a human or non-human mammal a immunomodulatory pharmaceutical composition according to any one of embodiments 57-60.

Embodiment 62

A method for modulating the immune response in a mammal to at least one preselected antigen or immunogen including co-administering to a human or non-human mammal
(a) at least substantially pure alpha-synuclein protein or a fragment thereof and
(b) at least one preselected antigen or immunogen, which is not a human or non-human mammalian alpha-synuclein protein or a fragment thereof. In one variation, the at least one preselected antigen or at least one preselected immunogen does not comprise a synuclein protein and/or does not comprise a fragment of a synuclein protein.

Embodiment 63

The method embodiment 62, further including co-administering at least partially purified human or non-human mammalian HLA protein or fragments thereof to the human or non-human mammal, wherein the at least one preselected antigen or immunogen does not include human or non-human mammalian HLA protein or fragments thereof.

Embodiment 64

The method embodiment 62, wherein HLA protein or fragments thereof are not co-administered to the human or non-human mammal.

Embodiment 65

A method for manufacturing an immunomodulatory pharmaceutical composition including the steps of:
providing at least substantially purified human or non-human mammalian alpha-synuclein protein or a fragment thereof;
providing at least one preselected antigen or immunogen, which is not a human or non-human mammalian alpha-synuclein protein or a fragments thereof; and
mixing the at least substantially purified mammalian alpha-synuclein protein or fragments thereof and the at least one preselected antigen or immunogen.

Embodiment 66

The method embodiment 65, further including:
providing at least partially purified human or non-human mammalian HLA protein or fragments thereof, and
wherein said mixing step further includes mixing the provided at least substantially pure alpha-synuclein protein or fragments thereof, the at least one preselected antigen or immunogen, and the at least partially purified human or non-human mammalian HLA protein or fragments thereof, and
wherein the at least one preselected antigen or immunogen is not a human or non-human mammalian HLA protein or fragment thereof.

In one variation, the at least one preselected antigen or immunogen is not an HLA protein or fragment thereof.

Embodiment 67

Either of embodiments 66 and 67, further including providing at least one pharmaceutically acceptable excipient, and mixing said at least one pharmaceutical excipient with the other mixed components of said embodiments.

Embodiment 68

A pharmaceutical composition including a mammalian alpha-synuclein, such as human alpha-synuclein protein, or a substantial fragment thereof. The alpha-synuclein protein or substantial fragment thereof may be recombinant. In one variation, the pharmaceutical composition consists essentially of a mammalian alpha-synuclein, such as human alpha-synuclein protein, or a substantial fragment thereof. In another variation, the pharmaceutical composition consists essentially of a mammalian alpha-synuclein, such as human alpha-synuclein protein, or a substantial fragment thereof and at least one preselected antigen or immunogen. The compositions may further include one or more pharmaceutically-acceptable excipients. The compositions may be parenteral or non-parenteral formulations. The compositions may, for example, be oral pharmaceutical compositions (formulated for oral administration (ingestion)) or in formulated in any manners described in this disclosure. The compositions may be in a solid dosage form, such as a powder, tablet or capsule. The compositions may be in a liquid form for either parenteral or non-parental administration. The compositions may be in liquid form for administration by injection.

The at least one preselected antigen or immunogen of various embodiments may, for example, be or include a peptide such as a synthetic peptide. The at least one preselected antigen or immunogen may, for example, be or include a protein such as an at least substantially purified protein, such as but not limited to an at least substantially purified recombinant protein. The at least one preselected antigen or immunogen may be or include a recombinant protein or a recombinant protein fragment of a full-length protein. Wherever throughout this disclosure an embodiment refers to a peptide antigen, it should be understood that corresponding embodiments directed to protein antigens are also intended to be disclosed and vice versa.

The at least one preselected peptide/protein antigen or immunogen may, for example, be or include a self-antigen of a human or non-human mammal, for example, a self-antigen associated with an autoimmune disease. The at least one preselected peptide/protein antigen or immunogen may, for example, be or include a cancer-associated antigen or an antigen preferentially expressed on cancer cells versus normal cells of a human or non-human mammal. The at least one preselected peptide/protein antigen may, for example, be or include a viral antigen, for example, of a pathogenic virus, such as a pathogenic virus that currently infects the subject or has previously infected the subject. For example, the virus may be Hepatitis B and the at least one preselected antigen may be one or more of HBsAg (surface antigen, S-protein) such as SEQ ID NO: 37 (adw serotype) and/or SEQ ID NO: 38 (adr serotype), HB pre-S1 protein (SEQ ID NO: 39), HB pre-S2 protein (SEQ ID NO: 40), HBeAg (HepB envelope antigen; e.g., SEQ ID NO: 41), and HBcAg (HepB core antigen; e.g. SEQ ID NO: 42).

The at least one preselected antigen that is or includes a self-antigen may be or include S-antigen, such as human S-antigen (SEQ ID NO: 4 or SEQ ID NO: 5) and/or a protein or peptide fragment thereof such as a synthetic peptide fragment. Immunomodulatory pharmaceutical composition embodiments of the invention including such antigens may be administered for the treatment of uveitis or AMD in a human or non-human mammal. In a particular embodiment, the peptide is or includes a fragment of S-antigen such as SEQ ID NO: 6 or SEQ ID NO: 7. Other synthetic peptides derived from or related to human S-antigen that may be used include:

| | |
|---|---|
| B27PD: | SEQ ID NO: 8 |
| Peptide 2 (P2): | SEQ ID NO: 9 |
| Peptide 6 (P6): | SEQ ID NO: 10 |
| Peptide 8 (P8): | SEQ ID NO: 11 |
| Peptide 29 (P29): | SEQ ID NO: 12 |
| Peptide 31 (P31): | SEQ ID NO: 13 |
| PDS-Ag: | SEQ ID NO: 14 |

The peptides may, for example, be the only preselected antigens or they may be used in any combination in the immunomodulatory compositions.

In certain embodiments, the patient has early AMD, characterized by medium drusen (63-125 μm) without pigmentary abnormalities thought to be related to AMD. In other embodiments, the patient has intermediate AMD, characterized by large drusen or with pigmentary abnormalities associated with at least medium drusen. In still other embodiments, the patient has late AMD, characterized by lesions associated with neovascular AMD or geographic atrophy. Drusen, which are yellow or white accumulations of extracellular material that build up between Bruch's membrane and the retinal pigment epithelium of the eye, can be measured by any technique known by the skilled artisan. In certain embodiments, drusen volumes are measured by spectral domain optical coherence tomography (SD-OCT). In other embodiments, the patient has wet AMD which may be associated with choroidal neovascularization (CNV).

A related embodiment provides a method for treating AMD in a human or non-human mammalian subject that includes administering any of said immunomodulatory pharmaceutical compositions to the subject. In various embodiments, the result obtained by treatment of AMD or uveitis includes cessation and/or slowing of disease progression, for example, progression from early AMD to intermediate AMD, or progression from intermediate AMD to late AMD, or cessation or slowing of progression to wet AMD, or cessation and/or slowing of neovascularization in wet AMD.

Another embodiment of the invention provides immunomodulatory pharmaceutical compositions according to the invention for the treatment of multiple sclerosis in a mammalian subject, such as a human patient, in which the at least one preselected antigen is or includes myelin basis protein (MBP) such as human myelin basis protein (for example, Genbank Accession No. AAC41944 myelin basic protein [*Homo sapiens*] SEQ ID NO: 15) and/or one or more fragments thereof, such as synthetic peptides. A related embodiment provides a method for treating multiple sclerosis in a human or non-human mammalian subject that includes administering said immunomodulatory composition to the subject.

Another embodiment of the invention provides an immunomodulatory pharmaceutical composition according to the invention for the treatment of rheumatoid arthritis in a human or non-human mammalian subject in which the at least one preselected antigen of the composition is or includes type II collagen such as human type II collagen protein (for example, Genbank Accession No. AAC41772 alpha-1 type II collagen [*Homo sapiens*]; SEQ ID NO:16) and/or one or more peptide fragments thereof, such as synthetic peptides. A related embodiment provides a method for treating rheumatoid arthritis in a human or non-human mammalian subject that includes administering said immunomodulatory composition to the subject.

Still further provided are immunomodulatory composition and a method embodiments for the amelioration of treatment-limiting immune reactivity in a mammalian subject, such as a human patient, that develops against a therapeutic protein that has been administered to the subject, such as a therapeutic antibody, e.g., a monoclonal antibody, such as Herceptin® (trastuzumab) or Avastin® (bevacizumab), or a soluble receptor, a growth factor, or an enzyme such as in enzyme replacement therapy. In this case, the at least one preselected antigen of the composition and method embodiments may, for example, be or include the therapeutic protein or one or more fragments thereof, or one or more peptides representing at least a portion of the amino acid sequence of the therapeutic protein.

At least partially purified HLA protein may, for example, be or include at least partially purified mammalian HLA protein. At least partially purified mammalian HLA protein may, for example, be or include at least partially purified human HLA protein. At least partially purified HLA protein may, for example, be or include one or more of HLA-A, HLA-B, HLA-C and HLA-G protein. At least partially purified HLA protein may, for example, be or include HLA Class II protein.

Alpha-synuclein and/or HLA and/or any proteins of embodiments of the invention may, for example, be recombinant or may be purified from tissue.

The immunomodulatory pharmaceutical composition may, for example, be in liquid form or in a solid/dry form such as in a powder or tablet form. The immunomodulatory pharmaceutical compositions may be parenteral or non-parenteral compositions. The immunomodulatory pharmaceutical compositions may, for example, be injectable compositions. The immunomodulatory pharmaceutical compositions may, for example, be orally administrable compositions. Administration to a subject may be by any route, such as parenteral or non-parenteral or a combination of routes. Administration may, for example, be made via injection or oral administration (ingestion) or by direct delivery to any part/section of the alimentary canal. Solid pharmaceutical compositions for oral administration via ingestion such as tablets or capsule may, for example, be enteric coated or otherwise formulated to prevent or minimize dissolution in the stomach but allow dissolution in the small intestine. Compositions for oral administration via ingestion may, for example, comprise or be co-administered with an antacid or other acid-reducing agent, such as omeprazole.

The resultant modulation of the immune response may be immunosuppressive, e.g., at least partially tolerance-inducing, with respect to the at least one preselected antigen or immunogen, or the resultant modulation of the immune response is immunostimulatory with respect to the at least one preselected antigen or immunogen.

In a variation of any of the embodiments presented herein, the pharmaceutical composition or mixture excludes (does not include) beta-2 microglobulin.

Still further embodiments of the invention are directed to methods and compositions for preventing and/or treating Hepatitis B infections, such as chronic Hepatitis B infections, Hepatitis B-associated liver diseases and/or Hepatitis B-associated cancers such as hepatocellular carcinoma (HCC), in non-human mammals and human patients.

Two studies were previously carried out with oral administration of HB SAg for treatment of patients with chronic Hepatitis B virus ("HBV," "HepB") infection. In Safadi et al. 2003 (Am J Gastroenterology 98: 2505-2515), a mixture of HB SAg+preS1+preS2 proteins was administered 3 times a week to a total of 42 chronic HBV patients. A significant drop in viral loads was seen for 15 out of 49 patients, and HB SAg and HBcAg biopsy scores were improved in 41% and 57% respectively. More interestingly, among the patients treated, 19 were HBeAg positive, the significance being that the presence of this marker is an indication that the patient has a higher risk for development of hepatocellular carcinoma (reviewed in Sharma et al. 2005). One criteria for successful treatment is loss of this marker and. indeed, out of the 19 HBeAg patients treated, 5 of them turned HBeAg negative and 4 of these 5 developed anti-HBeAg antibodies, thereby converting from what is termed a chronic carrier into an inactive carrier. Inactive carriers are considered to be in an essentially benign infected state associated with only a very low propensity for developing hepatocellular carcinoma (Sharma et al. 2005). In addition, another characteristic of the potential for cancer development over time is the change in a patient's profile where Th1 responses are reduced and Th2 responses increase. The effects of the oral treatment described in Safadi et al. resulted in 17/27 patients showing an increases in IFN-gamma secretion (an increase in a Th1 response) and 13/27 patients showing a reduction of IL10 secretion (a decrease in a Th2 response) thus showing a reversal in markers for progression towards development of hepatocellular carcinoma. In addition, 21/27 of the patients showed an increased HB SAg specific T cell proliferation, a potentially further indication that the recipients were mounting an effective Th1 response to HBV.

In a similar but separate study that was part of a limited clinical trial of 14 patients (Israeli et al., Liver International 2004 24; 295-307), a mixture of HB SAg+preS1+preS2 protein supplemented by the addition of liver extracted proteins was used. Due to the smaller size of the trial, only 4 of the 14 patients were HBeAg positive and consequently no patients were seen to seroconvert (the corresponding rate in the previous trial with 19 HBeAg patients would have predicted only 1 out of 4 at most to seroconvert from HBeAg positive to HBeAg negative). A rebalancing of the Th2 response compared to the Th1 response was also observed in this trial. Prior to treatment, 6 of the patients had elevated levels of IL-10. All 6 reverted to lower levels after treatment, and 5 out of 14 patients showed an increase in IFN-gamma secreting cells. Similar to the earlier study, in this clinical trial, 6 out of 10 patients showed an increase in antigen-specific T cell responses after treatment.

One embodiment of the invention provides a method for preventing or treating Hepatitis B infection, such as chronic Hepatitis B infection, Hepatitis B-associated liver disease and/or Hepatitis B-associated cancer such as hepatocellular carcinoma (HCC), in a non-human mammal and human patients, which method includes:

co-administering to the non-human mammal or human patient, for example, via oral administration:
(i) one or more HepB antigens such as one or more preselected HepB antigens, for example HepB proteins or peptides that are recombinantly or synthetically manufactured; and
(ii) one or more of: heat-treated blood (HTB) or a heat-treated RBC blood fraction, such as autologous or heterologous (from the same species of mammal or a different species of mammal), a cell membrane fraction of the foregoing, a protein extract of any of the foregoing, alpha-synuclein protein, such as mammalian alpha-synuclein protein, such as human alpha-synuclein protein, or fragments thereof of any of said alpha-synucleins. The utilized components of (i) and (ii) may be mixed together or provided as mixed and administered as one composition or may be co-administered as separate compositions.

The mammal or human may, for example, be currently infected with Hepatitis B virus, such as chronically infected with the virus, or was previously but not currently infected with Hepatitis B virus. Treatment of a chronic or active HepB infection can result in conversion to an inactive carrier state. In subjects with HCC, treatment can shift the immune response toward Th1 and prevent/delay progression of the HCC. In HBV infected subjects, treatment can prevent or delay the progression of HBV-associated liver diseases and progression to cancers such as HCC.

A related embodiment of the invention provides a pharmaceutical composition, such as an oral pharmaceutical composition for preventing or treating Hepatitis B infection, such as chronic Hepatitis B infection, Hepatitis B-associated liver disease and/or Hepatitis B-associated cancer such as hepatocellular carcinoma (HCC), in a non-human mammal and human patients, which composition includes:
(i) one or more HepB antigens such as one or more preselected HepB antigens, for example HepB proteins or peptides that are recombinantly or synthetically manufactured; and
(ii) one or more of: heat-treated blood (HTB) or a heat-treated RBC blood fraction, such as autologous or heterologous (from the same species of mammal or a different species of mammal), a cell membrane fraction of the foregoing, a protein extract of any of the foregoing, alpha-synuclein protein, such as mammalian alpha-synuclein protein, such as human alpha-synuclein protein, or fragments thereof of any of said alpha-synucleins.

The one or more Hepatitis B antigens in the preceding embodiments may, for example, be or include one or more (in any combination) of HBsAg (surface antigen, S-protein) such as SEQ ID NO: 37 (adw serotype) and/or SEQ ID NO: 38 (adr serotype), HB pre-S1 protein (SEQ ID NO: 39), HB pre-S2 protein (SEQ ID NO: 40), HBeAg (HepB envelope antigen; e.g., SEQ ID NO: 41), and HBcAg (HepB core antigen; e.g. SEQ ID NO: 42); recombinant forms of each are well known and commercially available. Alpha-synuclein in these embodiments may, for example, be recombinant (such as recombinant human alpha-synuclein, SEQ ID NO: 3) or purified from a tissue source. The Hepatitis B antigen(s) and alpha-synuclein(s) may, for example, each be provided in an at least substantially pure form for use in the embodiments.

The measurement of immune reactivity to selected antigens is a common practice in either diagnosing the presence of a disease state or delineating the stage or progression of a disease state. An example of the former is establishing whether an individual has been exposed to a particular antigen such as a viral, fungal or environmental agent. An example of the latter is the status of infection in a person exposed to *Mycobacterium tuberculosis* (TB) where different immune reactions are characteristic of different stages. For diagnostic purposes, the enhancement of immune reactivity by the presented invention may offer increased sensitivity where exposure to selected antigens can be detected at an earlier time point and enhanced detection of positive responses over background, thereby permitting determinations of positivity in otherwise ambiguous circumstances.

Accordingly, another embodiment of the invention provides an assay method for determining whether a sample of cells mounts an antigen-specific response to one or more preselected antigens and/or for quantifying the extent to which a sample of cells mounts an antigen-specific response to one or more preselected antigens, said method embodiment including the steps of: providing an isolated sample of cells, such as a sample of blood cells, such as whole blood, or a white blood cell fraction or PBMCs or T-cells; providing alpha-synuclein such as mammalian alpha-synuclein such as human alpha-synuclein and/or a fragment of any of the foregoing; providing at least one such as one preselected antigen, such as but not limited to an antigen which is a synthetic or recombinant peptide or protein; contacting the sample of cells with both the alpha-synuclein (any of the aforementioned varieties) and/or fragments thereof and the at least one preselected antigen; and measuring the resulting response of the sample of cells, for example, by quantifying the release of or increase of gene expressions of one or more cytokines, such as interferon gamma, for example using conventional and commercially available means such as ELISA assays for protein quantitation or quantitative RT-PCR for quantification of gene expression. The sample of cells may, for example, be obtained from a non-human mammal or a human. The synuclein or fragments thereof and the at least one preselected antigen may, for example, be mixed with each other (or be premixed) before being contacted with, such being added to, the sample of cells. Parallel steps may be run with all of the same components except for, i.e., excluding, the at least one preselected antigen (and optionally using a neutral "dummy antigen" in its place) as a control arm with the final measurements used as a negative control for the presumptive antigen stimulation arm.

A related embodiment of the invention provides an assay composition that includes, as mixture, an isolated sample of cells obtained from a subject, such as a sample of blood cells, such as whole blood, or a white blood cell fraction or PBMCs, said cells being, for example, non-human mammalian cells or human cells; alpha-synuclein such as mammalian alpha-synuclein such as human alpha-synuclein and/or a fragment of any of the foregoing; and at least one such as one preselected antigen, such as but not limited to an antigen which is a synthetic or recombinant peptide or protein.

In the aforementioned assay method and assay composition embodiments, the at least one preselected antigen may, for example, be or include an antigen of or associated with a pathogenic cellular organism such as a bacteria, fungi, amoeba or a virus. Antigen-specific reactivity detected from the sample of cells by the measuring step is indicative or strongly predictive that the subject from which the sample was obtained is currently infected with the pathogen. In this manner, a diagnosis can be provided. The at least one preselected antigen may, for example, be or include one or at least one protein/peptide antigen of *Mycobacterium tuberculosis* bacterium, for example, ESAT-6, or a peptide fragment of said antigen, for example, one or more fragments of ESAT-6, and may, for example, be or include one or more synthetic peptides or recombinant proteins. For example, full-length ESAT-6 protein may be used (such as SEQ ID NO: 17 herein), and/or any of the *Mycobacterium tuberculosis* ESAT-6 derived peptide antigens disclosed in U.S. Pat. No. 7,632,646 (such as SEQ ID NOS: 18-25 herein) may be used, and/or any of the non-ESAT-6 antigens in Mustafa et al., Clinical Infectious Diseases 2000; 30 (Suppl 3): S201-5 (such as SEQ ID NOS: 26-36 herein) may be used, each alone or in any combination.

The proteins used in various embodiments of the invention, such as HLA proteins and alpha-synuclein protein may, for example, be recombinant or may be purified from biological tissue sources, such as blood. In either case, the proteins may be at least substantially purified and/or at least substantially pure. By "at least substantially purified" and "at least substantially pure" it is intended is that the recited composition(s) need not be perfectly purified or perfectly pure. A fragment of a protein may, for example, include at least 5, such as at least 10, consecutive amino acids of the amino sequence of the protein but less than the full length sequence of the protein. A fragment of a protein may, for example, comprise consecutive amino sequence of the protein which is less than the full length of the protein, for example, 10-99% of the full length of the protein or any subrange of percentages therein, such as 10-90%, or any percent figures therein that correspond to any of the non-full length subsequences (of consecutive amino acids) of the protein.

Synthetic peptides used in the embodiments of the invention may, for example, be in the range of 5-40 amino acids long or any subrange therein or any number of amino acids within said range. For example, the synthetic peptides may be 10-30 amino acids long, 10-25 amino acids long, 10-20 amino acids long or 10-16 amino acids long.

As used herein, the term antigen means a molecule that presents one or more immune epitopes. Such epitopes, and thus the antigens themselves, may be immune reactivity-promoting (immunostimulatory; pro-effector T-cell) or immune suppression-promoting (immunosuppressive; pro-regulatory T-cell).

The immunogen may, for example, be a vaccine immunogen. The vaccine immunogen may, for example, be an infectious disease immunogen or a tumor/cancer antigen vaccine immunogen. The infectious disease immunogen may, for example, be a vaccine immunogen against a cellular or viral pathogen, may for example be a live or killed/inactivated form of the pathogen or a derivative/extract thereof, and/or may for example include or consist of one or more purified antigens such as synthetic antigen molecules for the pathogen, such as synthetic peptides or recombinant proteins. The tumor/cancer vaccine immunogen may, for example, include or consist of cancer cells, parts of cancer cells, or pure tumor/cancer antigens isolated from the cells or produced synthetically, such as, without limitation, synthetic peptides or recombinant proteins.

Each of the patents and other publications cited in this disclosure is hereby incorporated by reference in its entirety.

Although the foregoing description is directed to preferred embodiments of the invention, it is noted that other variations and modifications will be apparent to those skilled in the art, and may be made without departing from the spirit or scope of the invention. Wherever in this disclosure the terms include(s)/including or comprise(s)/comprising have been used, it should be understood that corresponding embodiments and disclosures reciting consist(s)/consisting and consist(s)/consisting essentially of are also taught.

Moreover, features described in connection with one embodiment of the invention may be used in conjunction or combination with other embodiments, even if not explicitly stated above.

---

What is claimed is:

1. An immunomodulatory pharmaceutical composition comprising:
   (a) at least substantially pure alpha-synuclein protein; and
   (b) at least one preselected antigen or immunogen, which is not a human or non-human mammalian alpha-synuclein protein or a fragment thereof.

2. The immunomodulatory pharmaceutical composition of claim 1, further comprising at least partially purified human or non-human mammalian HLA protein or fragments thereof, wherein the at least one preselected antigen or immunogen does not comprise human or non-human mammalian HLA protein or fragments thereof.

3. The immunomodulatory pharmaceutical composition of claim 1, wherein the at least one preselected antigen or immunogen comprises a synthetic peptide.

4. The immunomodulatory pharmaceutical composition of claim 1, wherein the at least one preselected antigen or immunogen comprises an at least substantially purified protein.

5. The immunomodulatory pharmaceutical composition of claim 4, wherein the at least substantially purified protein is a recombinant protein.

6. The immunomodulatory pharmaceutical composition of claim 1, consisting essentially of:
   (a) at least substantially pure alpha-synuclein protein; and
   (b) at least one preselected antigen or immunogen, which is not a human or non-human mammalian alpha-synuclein protein or a fragment thereof.

7. The immunomodulatory pharmaceutical composition of claim 6, wherein the at least one preselected antigen or immunogen comprises a synthetic peptide.

8. The immunomodulatory pharmaceutical composition of claim 6, wherein the at least one preselected antigen or immunogen comprises an at least substantially purified protein.

9. The immunomodulatory pharmaceutical composition of claim 8, wherein the at least substantially purified protein is a recombinant protein.

10. The immunomodulatory pharmaceutical composition of claim 1, wherein the at least one preselected antigen or immunogen comprises a self-antigen of a human or non-human mammal.

11. The immunomodulatory pharmaceutical composition of claim 9, wherein the self-antigen is associated with an autoimmune disease.

12. The immunomodulatory pharmaceutical composition of claim 1, wherein the at least one preselected antigen or immunogen comprises a cancer-associated antigen or an antigen preferentially expressed on cancer cells versus normal cells of a human or non-human mammal.

13. The composition of claim 1, further comprising at least one pharmaceutically acceptable excipient.

14. The composition of claim 1, wherein the at least one preselected antigen or immunogen does not comprise human or non-human mammalian HLA protein or fragments thereof.

15. The composition of claim 6, wherein the at least one preselected antigen or immunogen does not comprise human or non-human mammalian HLA protein or fragments thereof.

16. A method for modulating the immune response in a mammal to at least one preselected antigen comprising administering to a human or non-human mammal the immunomodulatory pharmaceutical composition of claim 1.

17. A method for modulating the immune response in a mammal to at least one preselected antigen comprising administering to a human or non-human mammal the immunomodulatory pharmaceutical composition of claim 6.

18. A method for manufacturing an immunomodulatory pharmaceutical composition comprising the steps of:
   providing at least substantially purified human or non-human mammalian alpha-synuclein protein;
   providing at least one preselected antigen or immunogen, which is not a human or non-human mammalian alpha-synuclein protein or a fragment thereof; and
   mixing the at least substantially purified mammalian alpha-synuclein protein and the at least one preselected antigen or immunogen.

19. The method of claim 18, wherein the at least one preselected antigen or immunogen comprises a synthetic peptide.

20. The method of claim 18, wherein the at least one preselected antigen or immunogen comprises an at least substantially purified protein.

21. The method of claim 20, wherein the at least substantially purified protein is a recombinant protein.

22. The method of claim 18, wherein the at least substantially purified human or non-human mammalian alpha-synuclein protein comprises recombinant alpha-synuclein protein.

23. The method of claim 22, wherein the at least one preselected antigen or immunogen comprises a synthetic peptide.

24. The method of claim 22, wherein the at least one preselected antigen or immunogen comprises an at least substantially purified protein.

25. The method of claim 24, wherein the at least substantially purified protein is a recombinant protein.

26. The method of claim 18, further comprising the step of:
   providing at least partially purified human or non-human mammalian HLA protein,
   wherein said mixing step further comprises mixing the provided at least substantially pure alpha-synuclein protein, the at least one preselected antigen or immunogen, and the at least partially purified human or non-human mammalian HLA protein, and
   wherein the at least one preselected antigen or immunogen is not a human or non-human mammalian HLA protein or fragment thereof.

* * * * *

SEQUENCE LISTING

```
<160> NUMBER OF SEQ ID NOS: 42

<210> SEQ ID NO 1
<211> LENGTH: 284
<212> TYPE: PRT
<213> ORGANISM: Homo sapiens

<400> SEQUENCE: 1

Gly Ser His Ser Met Arg Tyr Phe Tyr Thr Ala Met Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Cys Lys Thr Asn Thr Gln Thr Tyr Arg Glu Ser Leu Arg Asn
65                  70                  75                  80

Leu Arg Gly Tyr Tyr Asn Gln Ser Glu Ala Gly Ser His Thr Leu Gln
                85                  90                  95

Arg Met Tyr Gly Cys Asp Val Gly Pro Asp Gly Arg Leu Leu Arg Gly
            100                 105                 110

His Asp Gln Tyr Ala Tyr Asp Gly Lys Asp Tyr Ile Ala Leu Asn Glu
        115                 120                 125

Asp Leu Ser Ser Trp Thr Ala Ala Asp Thr Ala Ala Gln Ile Thr Gln
    130                 135                 140

Arg Lys Trp Glu Ala Ala Arg Glu Ala Glu Gln Leu Arg Ala Tyr Leu
145                 150                 155                 160

Glu Gly Leu Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Gly Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Ser Thr Ile Pro Ile
        275                 280

<210> SEQ ID NO 2
<211> LENGTH: 313
<212> TYPE: PRT
<213> ORGANISM: Homo sapiens

<400> SEQUENCE: 2

Gly Ser His Ser Met Arg Tyr Phe Ser Ala Ala Val Ser Arg Pro Gly
1               5                   10                  15
```

```
Arg Gly Glu Pro Arg Phe Ile Ala Met Gly Tyr Val Asp Asp Thr Gln
            20                  25                  30

Phe Val Arg Phe Asp Ser Asp Ser Ala Cys Pro Arg Met Glu Pro Arg
        35                  40                  45

Ala Pro Trp Val Glu Gln Glu Gly Pro Glu Tyr Trp Glu Glu Glu Thr
 50                  55                  60

Arg Asn Thr Lys Ala His Ala Gln Thr Asp Arg Met Asn Leu Gln Thr
 65                  70                  75                  80

Leu Arg Gly Tyr Tyr Asn Gln Ser Glu Ala Ser Ser His Thr Leu Gln
                85                  90                  95

Trp Met Ile Gly Cys Asp Leu Gly Ser Asp Gly Arg Leu Leu Arg Gly
            100                 105                 110

Tyr Glu Gln Tyr Ala Tyr Asp Gly Lys Asp Tyr Leu Ala Leu Asn Glu
        115                 120                 125

Asp Leu Arg Ser Trp Thr Ala Ala Asp Thr Ala Ala Gln Ile Ser Lys
130                 135                 140

Arg Lys Cys Glu Ala Ala Asn Val Ala Glu Gln Arg Arg Ala Tyr Leu
145                 150                 155                 160

Glu Gly Thr Cys Val Glu Trp Leu His Arg Tyr Leu Glu Asn Gly Lys
                165                 170                 175

Glu Met Leu Gln Arg Ala Asp Pro Pro Lys Thr His Val Thr His His
            180                 185                 190

Pro Val Phe Asp Tyr Glu Ala Thr Leu Arg Cys Trp Ala Leu Gly Phe
        195                 200                 205

Tyr Pro Ala Glu Ile Ile Leu Thr Trp Gln Arg Asp Gly Glu Asp Gln
210                 215                 220

Thr Gln Asp Val Glu Leu Val Glu Thr Arg Pro Ala Gly Asp Gly Thr
225                 230                 235                 240

Phe Gln Lys Trp Ala Ala Val Val Pro Ser Gly Glu Glu Gln Arg
                245                 250                 255

Tyr Thr Cys His Val Gln His Glu Gly Leu Pro Glu Pro Leu Met Leu
            260                 265                 270

Arg Trp Lys Gln Ser Ser Leu Pro Thr Ile Pro Ile Met Gly Ile Val
        275                 280                 285

Ala Gly Leu Val Val Leu Ala Ala Val Val Thr Gly Ala Ala Val Ala
290                 295                 300

Ala Val Leu Trp Arg Lys Lys Ser Ser
305                 310

<210> SEQ ID NO 3
<211> LENGTH: 140
<212> TYPE: PRT
<213> ORGANISM: Homo sapiens

<400> SEQUENCE: 3

Met Asp Val Phe Met Lys Gly Leu Ser Lys Ala Lys Glu Gly Val Val
  1               5                  10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
 50                  55                  60

Asn Val Gly Gly Ala Val Val Thr Gly Val Thr Ala Val Ala Gln Lys
 65                  70                  75                  80
```

```
Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140
```

<210> SEQ ID NO 4
<211> LENGTH: 405
<212> TYPE: PRT
<213> ORGANISM: Homo sapiens

<400> SEQUENCE: 4

```
Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
                20                  25                  30

Arg Asp Tyr Ile Asp His Val Ser Gln Val Gln Pro Val Asp Gly Val
            35                  40                  45

Val Leu Val Asp Pro Asp Leu Val Lys Gly Lys Lys Val Tyr Val Thr
50                  55                  60

Leu Thr Cys Ala Phe Arg Tyr Gly Gln Glu Asp Val Asp Val Ile Gly
65                  70                  75                  80

Leu Thr Phe Arg Arg Asp Leu Tyr Phe Ser Arg Val Gln Val Tyr Pro
                85                  90                  95

Pro Val Gly Ala Ala Ser Thr Pro Thr Lys Leu Gln Glu Ser Leu Leu
            100                 105                 110

Lys Lys Leu Gly Gly Asn Thr Tyr Pro Phe Leu Leu Thr Phe Pro Asp
        115                 120                 125

Tyr Leu Pro Cys Ser Val Met Leu Gln Pro Ala Pro Gln Asp Ser Gly
    130                 135                 140

Lys Ser Cys Gly Val Asp Phe Glu Val Lys Ala Phe Ala Thr Asp Ser
145                 150                 155                 160

Thr Asp Ala Glu Glu Asp Lys Ile Pro Lys Lys Ser Ser Val Arg Tyr
                165                 170                 175

Leu Ile Arg Ser Val Gln His Ala Pro Leu Glu Met Gly Pro Gln Pro
            180                 185                 190

Arg Ala Glu Ala Thr Trp Gln Phe Phe Met Ser Asp Lys Pro Leu His
        195                 200                 205

Leu Ala Val Ser Leu Asn Arg Glu Ile Tyr Phe His Gly Glu Pro Ile
    210                 215                 220

Pro Val Thr Val Asp Val Thr Asn Asn Thr Glu Lys Thr Val Lys Lys
225                 230                 235                 240

Ile Lys Ala Cys Val Glu Gln Val Ala Asn Val Val Leu Tyr Ser Ser
                245                 250                 255

Asp Tyr Tyr Val Lys Pro Val Ala Met Glu Glu Ala Gln Glu Lys Val
            260                 265                 270

Pro Pro Asn Ser Thr Leu Thr Lys Thr Leu Thr Leu Leu Pro Leu Leu
        275                 280                 285

Ala Asn Asn Arg Glu Arg Arg Gly Ile Ala Leu Asp Gly Lys Ile Lys
    290                 295                 300

His Glu Asp Thr Asn Leu Ala Ser Ser Thr Ile Ile Lys Glu Gly Ile
```

```
                    305                 310                 315                 320

Asp Arg Thr Val Leu Gly Ile Leu Val Ser Tyr Gln Ile Lys Val Lys
                325                 330                 335

Leu Thr Val Ser Gly Phe Leu Gly Glu Leu Thr Ser Ser Glu Val Ala
                340                 345                 350

Thr Glu Val Pro Phe Arg Leu Met His Pro Gln Pro Glu Asp Pro Ala
                355                 360                 365

Lys Glu Ser Ile Gln Asp Ala Asn Leu Val Phe Glu Glu Phe Ala Arg
                370                 375                 380

His Asn Leu Lys Asp Ala Gly Glu Ala Glu Glu Gly Lys Arg Asp Lys
385                 390                 395                 400

Asn Asp Ala Asp Glu
                405

<210> SEQ ID NO 5
<211> LENGTH: 405
<212> TYPE: PRT
<213> ORGANISM: Homo sapiens

<400> SEQUENCE: 5

Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
                20                  25                  30

Arg Asp Tyr Ile Asp His Val Ser Gln Val Gln Pro Val Asp Gly Val
                35                  40                  45

Val Leu Val Asp Pro Asp Leu Val Lys Gly Lys Lys Val Tyr Val Thr
                50                  55                  60

Leu Thr Cys Ala Phe Arg Tyr Gly Gln Glu Asp Ile Asp Val Ile Gly
65                  70                  75                  80

Leu Thr Phe Arg Arg Asp Leu Tyr Phe Ser Arg Val Gln Val Tyr Pro
                85                  90                  95

Pro Val Gly Ala Ala Ser Thr Pro Thr Lys Leu Gln Glu Ser Leu Leu
                100                 105                 110

Lys Lys Leu Gly Ser Asn Thr Tyr Pro Phe Leu Leu Thr Phe Pro Asp
                115                 120                 125

Tyr Leu Pro Cys Ser Val Met Leu Gln Pro Ala Pro Gln Asp Ser Gly
                130                 135                 140

Lys Ser Cys Gly Val Asp Phe Glu Val Lys Ala Phe Ala Thr Asp Ser
145                 150                 155                 160

Thr Asp Ala Glu Glu Asp Lys Ile Pro Lys Lys Ser Ser Val Arg Leu
                165                 170                 175

Leu Ile Arg Lys Val Gln His Ala Pro Leu Glu Met Gly Pro Gln Pro
                180                 185                 190

Arg Ala Glu Ala Ala Trp Gln Phe Phe Met Ser Asp Lys Pro Leu His
                195                 200                 205

Leu Ala Val Ser Leu Asn Lys Glu Ile Tyr Phe His Gly Glu Pro Ile
                210                 215                 220

Pro Val Thr Val Thr Val Thr Asn Asn Thr Glu Lys Thr Val Lys Lys
225                 230                 235                 240

Ile Lys Ala Phe Val Glu Gln Val Ala Asn Val Val Leu Tyr Ser Ser
                245                 250                 255

Asp Tyr Tyr Val Lys Pro Val Ala Met Glu Glu Ala Gln Glu Lys Val
                260                 265                 270
```

```
Pro Pro Asn Ser Thr Leu Thr Lys Thr Leu Thr Leu Pro Leu Leu
            275                 280                 285

Ala Asn Asn Arg Glu Arg Arg Gly Ile Ala Leu Asp Gly Lys Ile Lys
    290                 295                 300

His Glu Asp Thr Asn Leu Ala Ser Ser Thr Ile Ile Lys Glu Gly Ile
305                 310                 315                 320

Asp Arg Thr Val Leu Gly Ile Leu Val Ser Tyr Gln Ile Lys Val Lys
                325                 330                 335

Leu Thr Val Ser Gly Phe Leu Gly Glu Leu Thr Ser Ser Glu Val Ala
                340                 345                 350

Thr Glu Val Pro Phe Arg Leu Met His Pro Gln Pro Glu Asp Pro Ala
            355                 360                 365

Lys Glu Ser Tyr Gln Asp Ala Asn Leu Val Phe Glu Glu Phe Ala Arg
        370                 375                 380

His Asn Leu Lys Asp Ala Gly Glu Ala Glu Glu Gly Lys Arg Asp Lys
385                 390                 395                 400

Asn Asp Val Asp Glu
                405

<210> SEQ ID NO 6
<211> LENGTH: 20
<212> TYPE: PRT
<213> ORGANISM: Artificial Sequence
<220> FEATURE:
<223> OTHER INFORMATION: Synthetic fragment of human S-antigen

<400> SEQUENCE: 6

Gly Glu Pro Ile Pro Val Thr Val Asp Val Thr Asn Asn Thr Glu Lys
1               5                   10                  15

Thr Val Lys Lys
            20

<210> SEQ ID NO 7
<211> LENGTH: 15
<212> TYPE: PRT
<213> ORGANISM: Artificial Sequence
<220> FEATURE:
<223> OTHER INFORMATION: Synthetic fragment of human S-antigen

<400> SEQUENCE: 7

Val Thr Val Asp Val Thr Asn Asn Thr Glu Lys Thr Val Lys Lys
1               5                   10                  15

<210> SEQ ID NO 8
<211> LENGTH: 14
<212> TYPE: PRT
<213> ORGANISM: Artificial Sequence
<220> FEATURE:
<223> OTHER INFORMATION: Synthetic HLA peptide B27PD

<400> SEQUENCE: 8

Ala Leu Asn Glu Asp Leu Ser Ser Trp Thr Ala Ala Asp Thr
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Synthetic fragment of human S-antigen

<400> SEQUENCE: 9
```

```
Ile Phe Lys Lys Ile Ser Arg Asp Lys Ser Val Thr Ile Tyr Leu
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic fragment of human S-antigen

<400> SEQUENCE: 10

Val Lys Gly Lys Lys Val Tyr Val Thr Leu Thr Cys Ala Phe Arg
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic fragment of human S-antigen

<400> SEQUENCE: 11

Tyr Gly Gln Glu Asp Val Asp Val Ile Gly Leu Thr Phe Arg Arg
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic fragment of human S-antigen

<400> SEQUENCE: 12

Leu Pro Leu Leu Ala Asn Asn Arg Glu Arg Arg Gly Ile Ala Leu
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic fragment of human S-antigen

<400> SEQUENCE: 13

Asp Thr Asn Leu Ala Ser Ser Thr Ile Ile Lys Glu Gly Ile Asp
1               5                   10                  15

<210> SEQ ID NO 14
<211> LENGTH: 14
<212> TYPE: PRT
<213> ORGANISM: Artificial Sequence
<220> FEATURE:
<223> OTHER INFORMATION: Synthetic peptide

<400> SEQUENCE: 14

Ala Leu Asn Glu Asp Leu Ser Ser Trp Thr Ala Ala Asp Thr
1               5                   10

<210> SEQ ID NO 15
<211> LENGTH: 203
<212> TYPE: PRT
<213> ORGANISM: Homo sapiens

<400> SEQUENCE: 15

Met Ala Ser Gln Lys Arg Pro Ser Gln Arg His Gly Ser Lys Tyr Leu
1               5                   10                  15
```

```
Ala Thr Ala Ser Thr Met Asp His Ala Arg His Gly Phe Leu Pro Arg
             20                  25                  30

His Arg Asp Thr Gly Ile Leu Asp Ser Ile Gly Arg Phe Phe Gly Gly
         35                  40                  45

Asp Arg Gly Ala Pro Lys Arg Gly Ser Gly Lys Val Pro Trp Leu Lys
     50                  55                  60

Pro Gly Arg Ser Pro Leu Pro Ser His Ala Arg Ser Gln Pro Gly Leu
 65                  70                  75                  80

Cys Asn Met Tyr Lys Asp Ser His His Pro Ala Arg Thr Ala His Tyr
                 85                  90                  95

Gly Ser Leu Pro Gln Lys Ser His Gly Arg Thr Gln Asp Glu Asn Pro
            100                 105                 110

Val Val His Phe Phe Lys Asn Ile Val Thr Pro Arg Thr Pro Pro Pro
        115                 120                 125

Ser Gln Gly Lys Gly Arg Gly Leu Ser Leu Ser Arg Phe Ser Trp Gly
    130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg His His His His His His
            195                 200

<210> SEQ ID NO 16
<211> LENGTH: 1487
<212> TYPE: PRT
<213> ORGANISM: Homo sapiens

<400> SEQUENCE: 16

Met Ile Arg Leu Gly Ala Pro Gln Ser Leu Val Leu Leu Thr Leu Leu
 1               5                  10                  15

Val Ala Ala Val Leu Arg Cys Gln Gly Gln Asp Val Gln Glu Ala Gly
             20                  25                  30

Ser Cys Val Gln Asp Gly Gln Arg Tyr Asn Asp Lys Asp Val Trp Lys
         35                  40                  45

Pro Glu Pro Cys Arg Ile Cys Val Cys Asp Thr Gly Thr Val Leu Cys
     50                  55                  60

Asp Asp Ile Ile Cys Glu Asp Val Lys Asp Cys Leu Ser Pro Glu Ile
 65                  70                  75                  80

Pro Phe Gly Glu Cys Cys Pro Ile Cys Pro Thr Asp Leu Ala Thr Ala
                 85                  90                  95

Ser Gly Gln Pro Gly Pro Lys Gly Gln Lys Gly Glu Pro Gly Asp Ile
            100                 105                 110

Lys Asp Ile Val Gly Pro Lys Gly Pro Pro Gly Pro Gln Gly Pro Ala
        115                 120                 125

Gly Glu Gln Gly Pro Arg Gly Asp Arg Gly Asp Lys Gly Glu Lys Gly
    130                 135                 140

Ala Pro Gly Pro Arg Gly Arg Asp Gly Glu Pro Gly Thr Pro Gly Asn
145                 150                 155                 160

Pro Gly Pro Pro Gly Pro Pro Gly Pro Pro Gly Pro Pro Gly Leu Gly
                165                 170                 175

Gly Asn Phe Ala Ala Gln Met Ala Gly Gly Phe Asp Glu Lys Ala Gly
            180                 185                 190
```

```
Gly Ala Gln Leu Gly Val Met Gln Gly Pro Met Gly Pro Met Gly Pro
            195                 200                 205

Arg Gly Pro Pro Gly Pro Ala Gly Ala Pro Gly Pro Gln Gly Phe Gln
            210                 215                 220

Gly Asn Pro Gly Glu Pro Gly Glu Pro Gly Val Ser Gly Pro Met Gly
225                 230                 235                 240

Pro Arg Gly Pro Pro Gly Pro Pro Gly Lys Pro Gly Asp Asp Gly Glu
                245                 250                 255

Ala Gly Lys Pro Gly Lys Ala Gly Glu Arg Gly Pro Pro Gly Pro Gln
                260                 265                 270

Gly Ala Arg Gly Phe Pro Gly Thr Pro Gly Leu Pro Gly Val Lys Gly
            275                 280                 285

His Arg Gly Tyr Pro Gly Leu Asp Gly Ala Lys Gly Glu Ala Gly Ala
            290                 295                 300

Pro Gly Val Lys Gly Glu Ser Gly Ser Pro Gly Glu Asn Gly Ser Pro
305                 310                 315                 320

Gly Pro Met Gly Pro Arg Gly Leu Pro Gly Glu Arg Gly Arg Thr Gly
                325                 330                 335

Pro Ala Gly Ala Ala Gly Ala Arg Gly Asn Asp Gly Gln Pro Gly Pro
            340                 345                 350

Ala Gly Pro Pro Gly Pro Val Gly Pro Ala Gly Gly Pro Gly Phe Pro
            355                 360                 365

Gly Ala Pro Gly Ala Lys Gly Glu Ala Gly Pro Thr Gly Ala Arg Gly
            370                 375                 380

Pro Glu Gly Ala Gln Gly Pro Arg Gly Glu Pro Gly Thr Pro Gly Ser
385                 390                 395                 400

Pro Gly Pro Ala Gly Ala Ser Gly Asn Pro Gly Thr Asp Gly Ile Pro
                405                 410                 415

Gly Ala Lys Gly Ser Ala Gly Ala Pro Gly Ile Ala Gly Ala Pro Gly
                420                 425                 430

Phe Pro Gly Pro Arg Gly Pro Pro Gly Pro Gln Gly Ala Thr Gly Pro
            435                 440                 445

Leu Gly Pro Lys Gly Gln Thr Gly Glu Pro Gly Ile Ala Gly Phe Lys
            450                 455                 460

Gly Glu Gln Gly Pro Lys Gly Glu Pro Gly Pro Ala Gly Pro Gln Gly
465                 470                 475                 480

Ala Pro Gly Pro Ala Gly Glu Glu Gly Lys Arg Gly Ala Arg Gly Glu
                485                 490                 495

Pro Gly Gly Val Gly Pro Ile Gly Pro Pro Gly Glu Arg Gly Ala Pro
            500                 505                 510

Gly Asn Arg Gly Phe Pro Gly Gln Asp Gly Leu Ala Gly Pro Lys Gly
            515                 520                 525

Ala Pro Gly Glu Arg Gly Pro Ser Gly Leu Ala Gly Pro Lys Gly Ala
            530                 535                 540

Asn Gly Asp Pro Gly Arg Pro Gly Glu Pro Gly Leu Pro Gly Ala Arg
545                 550                 555                 560

Gly Leu Thr Gly Arg Pro Gly Asp Ala Gly Pro Gln Gly Lys Val Gly
                565                 570                 575

Pro Ser Gly Ala Pro Gly Glu Asp Gly Arg Pro Gly Pro Pro Gly Pro
            580                 585                 590

Gln Gly Ala Arg Gly Gln Pro Gly Val Met Gly Phe Pro Gly Pro Lys
            595                 600                 605
```

```
Gly Ala Asn Gly Glu Pro Gly Lys Ala Gly Glu Lys Gly Leu Pro Gly
    610                 615                 620

Ala Pro Gly Leu Arg Gly Leu Pro Gly Lys Asp Gly Glu Thr Gly Ala
625                 630                 635                 640

Ala Gly Pro Pro Gly Pro Ala Gly Pro Ala Gly Glu Arg Gly Glu Gln
                645                 650                 655

Gly Ala Pro Gly Pro Ser Gly Phe Gln Gly Leu Pro Gly Pro Pro Gly
                660                 665                 670

Pro Pro Gly Glu Gly Gly Lys Pro Gly Asp Gln Gly Val Pro Gly Glu
            675                 680                 685

Ala Gly Ala Pro Gly Leu Val Gly Pro Arg Gly Glu Arg Gly Phe Pro
    690                 695                 700

Gly Glu Arg Gly Ser Pro Gly Ala Gln Gly Leu Gln Gly Pro Arg Gly
705                 710                 715                 720

Leu Pro Gly Thr Pro Gly Thr Asp Gly Pro Lys Gly Ala Ser Gly Pro
                725                 730                 735

Ala Gly Pro Pro Gly Ala Gln Gly Pro Pro Gly Leu Gln Gly Met Pro
                740                 745                 750

Gly Glu Arg Gly Ala Ala Gly Ile Ala Gly Pro Lys Gly Asp Arg Gly
            755                 760                 765

Asp Val Gly Glu Lys Gly Pro Glu Gly Ala Pro Gly Lys Asp Gly Gly
    770                 775                 780

Arg Gly Leu Thr Gly Pro Ile Gly Pro Pro Gly Pro Ala Gly Ala Asn
785                 790                 795                 800

Gly Glu Lys Gly Glu Val Gly Pro Pro Gly Pro Ala Gly Ser Ala Gly
                805                 810                 815

Ala Arg Gly Ala Pro Gly Glu Arg Gly Glu Thr Gly Pro Pro Gly Pro
            820                 825                 830

Ala Gly Phe Ala Gly Pro Pro Gly Ala Asp Gly Gln Pro Gly Ala Lys
    835                 840                 845

Gly Glu Gln Gly Glu Ala Gly Gln Lys Gly Asp Ala Gly Ala Pro Gly
                850                 855                 860

Pro Gln Gly Pro Ser Gly Ala Pro Gly Pro Gln Gly Pro Thr Gly Val
865                 870                 875                 880

Thr Gly Pro Lys Gly Ala Arg Gly Ala Gln Gly Pro Pro Gly Ala Thr
            885                 890                 895

Gly Phe Pro Gly Ala Ala Gly Arg Val Gly Pro Pro Gly Ser Asn Gly
    900                 905                 910

Asn Pro Gly Pro Pro Gly Pro Pro Gly Pro Ser Gly Lys Asp Gly Pro
                915                 920                 925

Lys Gly Ala Arg Gly Asp Ser Gly Pro Pro Gly Arg Ala Gly Glu Pro
930                 935                 940

Gly Leu Gln Gly Pro Ala Gly Pro Pro Gly Glu Lys Gly Glu Pro Gly
945                 950                 955                 960

Asp Asp Gly Pro Ser Gly Ala Glu Gly Pro Pro Gly Pro Gln Gly Leu
                965                 970                 975

Ala Gly Gln Arg Gly Ile Val Gly Leu Pro Gly Gln Arg Gly Glu Arg
            980                 985                 990

Gly Phe Pro Gly Leu Pro Gly Ser Gly Glu Pro Gly Lys Gln Gly
            995                 1000                1005

Ala Pro Gly Ala Ser Gly Asp Arg Gly Pro Pro Gly Pro Val Gly
    1010                1015                1020

Pro Pro Gly Leu Thr Gly Pro Ala Gly Glu Pro Gly Arg Glu Gly
```

-continued

```
            1025                1030                1035
Ser Pro Gly Ala Asp Gly Pro Pro Gly Arg Asp Gly Ala Ala Gly
        1040                1045                1050
Val Lys Gly Asp Arg Gly Glu Thr Gly Ala Val Gly Ala Pro Gly
        1055                1060                1065
Ala Pro Gly Pro Pro Gly Ser Pro Gly Pro Ala Gly Pro Thr Gly
        1070                1075                1080
Lys Gln Gly Asp Arg Gly Glu Ala Gly Ala Gln Gly Pro Met Gly
        1085                1090                1095
Pro Ser Gly Pro Ala Gly Ala Arg Gly Ile Gln Gly Pro Gln Gly
        1100                1105                1110
Pro Arg Gly Asp Lys Gly Glu Ala Gly Glu Pro Gly Glu Arg Gly
        1115                1120                1125
Leu Lys Gly His Arg Gly Phe Thr Gly Leu Gln Gly Leu Pro Gly
        1130                1135                1140
Pro Pro Gly Pro Ser Gly Asp Gln Gly Ala Ser Gly Pro Ala Gly
        1145                1150                1155
Pro Ser Gly Pro Arg Gly Pro Pro Gly Pro Val Gly Pro Ser Gly
        1160                1165                1170
Lys Asp Gly Ala Asn Gly Ile Pro Gly Pro Ile Gly Pro Pro Gly
        1175                1180                1185
Pro Arg Gly Arg Ser Gly Glu Thr Gly Pro Ala Gly Pro Pro Gly
        1190                1195                1200
Asn Pro Gly Pro Pro Gly Pro Pro Gly Pro Pro Gly Pro Gly Ile
        1205                1210                1215
Asp Met Ser Ala Phe Ala Gly Leu Gly Pro Arg Glu Lys Gly Pro
        1220                1225                1230
Asp Pro Leu Gln Tyr Met Arg Ala Asp Gln Ala Ala Gly Gly Leu
        1235                1240                1245
Arg Gln His Asp Ala Glu Val Asp Ala Thr Leu Lys Ser Leu Asn
        1250                1255                1260
Asn Gln Ile Glu Ser Ile Arg Ser Pro Glu Gly Ser Arg Lys Asn
        1265                1270                1275
Pro Ala Arg Thr Cys Arg Asp Leu Lys Leu Cys His Pro Glu Trp
        1280                1285                1290
Lys Ser Gly Asp Tyr Trp Ile Asp Pro Asn Gln Gly Cys Thr Leu
        1295                1300                1305
Asp Ala Met Lys Val Phe Cys Asn Met Glu Thr Gly Glu Thr Cys
        1310                1315                1320
Val Tyr Pro Asn Pro Ala Asn Val Pro Lys Lys Asn Trp Trp Ser
        1325                1330                1335
Ser Lys Ser Lys Glu Lys Lys His Ile Trp Phe Gly Glu Thr Ile
        1340                1345                1350
Asn Gly Gly Phe His Phe Ser Tyr Gly Asp Asp Asn Leu Ala Pro
        1355                1360                1365
Asn Thr Ala Asn Val Gln Met Thr Phe Leu Arg Leu Leu Ser Thr
        1370                1375                1380
Glu Gly Ser Gln Asn Ile Thr Tyr His Cys Lys Asn Ser Ile Ala
        1385                1390                1395
Tyr Leu Asp Glu Ala Ala Gly Asn Leu Lys Lys Ala Leu Leu Ile
        1400                1405                1410
Gln Gly Ser Asn Asp Val Glu Ile Arg Ala Glu Gly Asn Ser Arg
        1415                1420                1425
```

```
Phe Thr Tyr Thr Ala Leu Lys Asp Gly Cys Thr Lys His Thr Gly
    1430                1435               1440

Lys Trp Gly Lys Thr Val Ile Glu Tyr Arg Ser Gln Lys Thr Ser
    1445                1450               1455

Arg Leu Pro Ile Ile Asp Ile Ala Pro Met Asp Ile Gly Gly Pro
    1460                1465               1470

Glu Gln Glu Phe Gly Val Asp Ile Gly Pro Val Cys Phe Leu
    1475                1480               1485

<210> SEQ ID NO 17
<211> LENGTH: 95
<212> TYPE: PRT
<213> ORGANISM: Mycobacterium tuberculosis

<400> SEQUENCE: 17

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 18
<211> LENGTH: 20
<212> TYPE: PRT
<213> ORGANISM: Mycobacterium tuberculosis

<400> SEQUENCE: 18

Met Thr Glu Gln Gln Trp Asn Phe Ala Gly Ile Glu Ala Ala Ala Ser
1               5                   10                  15

Ala Ile Gln Gly
            20

<210> SEQ ID NO 19
<211> LENGTH: 24
<212> TYPE: PRT
<213> ORGANISM: Mycobacterium tuberculosis

<400> SEQUENCE: 19

Glu Ala Ala Ala Ser Ala Ile Gln Gly Asn Val Thr Ser Ile His Ser
1               5                   10                  15

Leu Leu Asp Glu Gly Lys Gln Ser
            20

<210> SEQ ID NO 20
<211> LENGTH: 24
<212> TYPE: PRT
<213> ORGANISM: Mycobacterium tuberculosis

<400> SEQUENCE: 20

Val Thr Ser Ile His Ser Leu Leu Asp Glu Gly Lys Gln Ser Leu Thr
1               5                   10                  15

Lys Leu Ala Ala Ala Trp Gly Gly
```

20

<210> SEQ ID NO 21
<211> LENGTH: 24
<212> TYPE: PRT
<213> ORGANISM: Mycobacterium tuberculosis

<400> SEQUENCE: 21

Gly Lys Gln Ser Leu Thr Lys Leu Ala Ala Trp Gly Gly Ser Gly
1               5                   10                  15

Ser Glu Ala Tyr Gln Gly Val Gln
            20

<210> SEQ ID NO 22
<211> LENGTH: 24
<212> TYPE: PRT
<213> ORGANISM: Mycobacterium tuberculosis

<400> SEQUENCE: 22

Ala Trp Gly Gly Ser Gly Ser Glu Ala Tyr Gln Gly Val Gln Gln Lys
1               5                   10                  15

Trp Asp Ala Thr Ala Thr Glu Leu
            20

<210> SEQ ID NO 23
<211> LENGTH: 24
<212> TYPE: PRT
<213> ORGANISM: Mycobacterium tuberculosis

<400> SEQUENCE: 23

Gln Gly Val Gln Gln Lys Trp Asp Ala Thr Ala Thr Glu Leu Asn Asn
1               5                   10                  15

Ala Leu Gln Asn Leu Ala Arg Thr
            20

<210> SEQ ID NO 24
<211> LENGTH: 24
<212> TYPE: PRT
<213> ORGANISM: Mycobacterium tuberculosis

<400> SEQUENCE: 24

Ala Thr Glu Leu Asn Asn Ala Leu Gln Asn Leu Ala Arg Thr Ile Ser
1               5                   10                  15

Glu Ala Gly Gln Ala Met Ala Ser
            20

<210> SEQ ID NO 25
<211> LENGTH: 24
<212> TYPE: PRT
<213> ORGANISM: Mycobacterium tuberculosis

<400> SEQUENCE: 25

Leu Ala Arg Thr Ile Ser Glu Ala Gly Gln Ala Met Ala Ser Thr Glu
1               5                   10                  15

Gly Asn Val Thr Gly Met Phe Ala
            20

<210> SEQ ID NO 26
<211> LENGTH: 15
<212> TYPE: PRT
<213> ORGANISM: Mycobacterium tuberculosis

<400> SEQUENCE: 26

```
Met Thr Glu Gln Gln Trp Asn Phe Ala Gly Ile Glu Ala Ala Ala
1               5                  10                  15

<210> SEQ ID NO 27
<211> LENGTH: 15
<212> TYPE: PRT
<213> ORGANISM: Mycobacterium tuberculosis

<400> SEQUENCE: 27

Ser Ala Ile Gln Gly Asn Val Thr Ser Ile His Ser Leu Leu Asp
1               5                  10                  15

<210> SEQ ID NO 28
<211> LENGTH: 15
<212> TYPE: PRT
<213> ORGANISM: Mycobacterium tuberculosis

<400> SEQUENCE: 28

Gln Lys Trp Asp Ala Thr Ala Thr Glu Leu Asn Asn Ala Leu Gln
1               5                  10                  15

<210> SEQ ID NO 29
<211> LENGTH: 15
<212> TYPE: PRT
<213> ORGANISM: Mycobacterium tuberculosis

<400> SEQUENCE: 29

Asn Asn Ala Leu Gln Asn Leu Ala Arg Thr Ile Ser Glu Ala Gly
1               5                  10                  15

<210> SEQ ID NO 30
<211> LENGTH: 15
<212> TYPE: PRT
<213> ORGANISM: Mycobacterium tuberculosis

<400> SEQUENCE: 30

Asn Leu Ala Arg Thr Ile Ser Glu Ala Gly Gln Ala Met Ala Ser
1               5                  10                  15

<210> SEQ ID NO 31
<211> LENGTH: 15
<212> TYPE: PRT
<213> ORGANISM: Mycobacterium tuberculosis

<400> SEQUENCE: 31

Trp Asn Phe Ala Gly Ile Glu Ala Ala Ala Ser Ala Ile Gln Gly
1               5                  10                  15

<210> SEQ ID NO 32
<211> LENGTH: 15
<212> TYPE: PRT
<213> ORGANISM: Mycobacterium tuberculosis

<400> SEQUENCE: 32

Glu Gly Lys Gln Ser Leu Thr Lys Leu Ala Ala Ala Trp Gly Gly
1               5                  10                  15

<210> SEQ ID NO 33
<211> LENGTH: 15
<212> TYPE: PRT
<213> ORGANISM: Mycobacterium tuberculosis

<400> SEQUENCE: 33

Tyr Gln Gly Val Gln Gln Lys Trp Asp Ala Thr Ala Thr Glu Leu
```

-continued

```
1               5                   10                  15
```

<210> SEQ ID NO 34
<211> LENGTH: 15
<212> TYPE: PRT
<213> ORGANISM: Mycobacterium tuberculosis

<400> SEQUENCE: 34

```
Asn Val Thr Ser Ile His Ser Leu Leu Asp Glu Gly Lys Gln Ser
1               5                   10                  15
```

<210> SEQ ID NO 35
<211> LENGTH: 15
<212> TYPE: PRT
<213> ORGANISM: Mycobacterium tuberculosis

<400> SEQUENCE: 35

```
Ile Glu Ala Ala Ala Ser Ala Ile Gln Gly Asn Val Thr Ser Ile
1               5                   10                  15
```

<210> SEQ ID NO 36
<211> LENGTH: 15
<212> TYPE: PRT
<213> ORGANISM: Mycobacterium tuberculosis

<400> SEQUENCE: 36

```
Thr Ala Thr Glu Leu Asn Asn Ala Leu Gln Asn Leu Ala Arg Thr
1               5                   10                  15
```

<210> SEQ ID NO 37
<211> LENGTH: 226
<212> TYPE: PRT
<213> ORGANISM: Hepatitis B virus

<400> SEQUENCE: 37

```
Met Glu Asn Ile Thr Ser Gly Leu Leu Gly Pro Leu Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Ser Phe Leu Gly Glu Ala Pro Val Cys
            35                  40                  45

Leu Gly Gln Asn Ser Gln Ser Pro Thr Arg Asn His Ser Pro Thr Ser
        50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

Gln Gly Asn Ser Met Phe Pro Ser Cys Cys Thr Lys Pro Thr Asp
        130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190
```

```
Ser Ala Ile Trp Met Ile Trp Tyr Trp Gly Pro Ser Leu Tyr Ser Ile
            195                 200                 205

Val Cys Pro Phe Thr Pro Leu Leu Gln Ile Phe Cys Cys Leu Trp Val
    210                 215                 220

Phe Ile
225

<210> SEQ ID NO 38
<211> LENGTH: 226
<212> TYPE: PRT
<213> ORGANISM: Hepatitis B virus

<400> SEQUENCE: 38

Met Glu Ser Thr Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Asn Phe Leu Gly Gly Ala Pro Thr Cys
            35                  40                  45

Pro Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Leu Pro Gly
            100                 105                 110

Thr Ser Thr Thr Ser Thr Gly Pro Cys Lys Thr Cys Thr Ile Pro Ala
        115                 120                 125

Gln Gly Thr Ser Met Phe Pro Ser Cys Cys Cys Thr Lys Pro Ser Asp
    130                 135                 140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Leu Leu
                165                 170                 175

Val Pro Phe Val Gln Trp Phe Ala Gly Leu Ser Pro Thr Val Trp Leu
            180                 185                 190

Ser Val Ile Trp Met Met Trp Tyr Trp Gly Pro Ser Leu Tyr Asn Ile
        195                 200                 205

Leu Ser Pro Phe Leu Pro Leu Leu Pro Ile Phe Phe Cys Leu Trp Val
    210                 215                 220

Tyr Ile
225

<210> SEQ ID NO 39
<211> LENGTH: 119
<212> TYPE: PRT
<213> ORGANISM: Hepatitis B virus

<400> SEQUENCE: 39

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Gly Ala Asn Ser Asn Asn Pro Asp Trp Asp Phe Asn Pro Asn
            35                  40                  45
```

```
Lys Asp His Trp Pro Glu Ala His Gln Val Gly Ala Gly Ala Phe Gly
 50                  55                  60

Pro Gly Phe Thr Pro Pro His Gly Gly Leu Leu Gly Trp Ser Pro Gln
 65                  70                  75                  80

Ala Gln Gly Ile Leu Thr Thr Val Pro Val Ala Pro Pro Pro Ala Ser
                 85                  90                  95

Thr Asn Arg Gln Ser Gly Arg Gln Pro Thr Pro Ile Ser Pro Pro Leu
            100                 105                 110

Arg Asp Ser His Pro Gln Ala
            115

<210> SEQ ID NO 40
<211> LENGTH: 55
<212> TYPE: PRT
<213> ORGANISM: Hepatitis B virus

<400> SEQUENCE: 40

Met Gln Trp Asn Ser Thr Thr Phe His Gln Ala Leu Leu Asp Pro Lys
 1               5                  10                  15

Val Arg Gly Leu Tyr Phe Pro Ala Gly Gly Ser Ser Ser Gly Thr Val
                20                  25                  30

Asn Pro Val Pro Thr Thr Ala Ser Pro Ile Ser Ser Ile Phe Ser Arg
            35                  40                  45

Thr Gly Asp Pro Ala Pro Asn
 50                  55

<210> SEQ ID NO 41
<211> LENGTH: 195
<212> TYPE: PRT
<213> ORGANISM: Hepatitis B virus

<400> SEQUENCE: 41

Ser Lys Leu Cys Leu Gly Trp Leu Trp Gly Met Asp Ile Asp Pro Tyr
 1               5                  10                  15

Lys Glu Phe Gly Ala Thr Val Glu Leu Leu Ser Phe Leu Pro Ser Asp
                20                  25                  30

Phe Phe Pro Ser Val Arg Asp Leu Leu Asp Thr Ala Ser Ala Leu Tyr
            35                  40                  45

Arg Glu Ala Leu Glu Ser Pro Glu His Cys Ser Pro His His Thr Ala
 50                  55                  60

Leu Arg Gln Ala Ile Leu Cys Trp Gly Glu Leu Met Thr Leu Ala Thr
 65                  70                  75                  80

Trp Val Gly Asn Asn Leu Glu Asp Pro Ala Ser Arg Asp Leu Val Val
                85                  90                  95

Asn Tyr Val Asn Thr Asn Val Gly Leu Lys Ile Arg Gln Leu Leu Trp
            100                 105                 110

Phe His Ile Ser Cys Leu Thr Phe Gly Arg Glu Thr Val Leu Glu Tyr
            115                 120                 125

Leu Val Ser Phe Gly Val Trp Ile Arg Thr Pro Pro Ala Tyr Arg Pro
            130                 135                 140

Pro Asn Ala Pro Ile Leu Ser Thr Leu Pro Glu Thr Thr Val Val Arg
145                 150                 155                 160

Arg Arg Asp Arg Gly Arg Ser Pro Arg Arg Arg Thr Pro Ser Pro Arg
                165                 170                 175

Arg Arg Arg Ser Pro Ser Pro Arg Arg Arg Ser Gln Ser Arg Glu
            180                 185                 190
```

```
Ser Gln Cys
        195

<210> SEQ ID NO 42
<211> LENGTH: 183
<212> TYPE: PRT
<213> ORGANISM: Hepatitis B virus

<400> SEQUENCE: 42

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Phe Arg Gln Leu Leu Trp Phe His Val Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```